United States Patent
Liu et al.

(10) Patent No.: US 11,744,870 B2
(45) Date of Patent: Sep. 5, 2023

(54) TRADITIONAL CHINESE MEDICINE COMPOSITION FOR TREATING METABOLIC SYNDROME AND PREPARATIONS THEREOF

(71) Applicants: JIANGSU JIUXU PHARMACEUTICAL CO., LTD., Jiangsu (CN); Hong Li, Jiangsu (CN)

(72) Inventors: Ximing Liu, Beijing (CN); Hong Li, Jiangsu (CN)

(73) Assignees: JIANGSU JIUXU PHARMACEUTICAL CO., LTD., Jiangsu (CN); Hong Li, Jiangsu (CN)

( * ) Notice: Subject to any disclaimer, the term of this patent is extended or adjusted under 35 U.S.C. 154(b) by 133 days.

(21) Appl. No.: 17/274,968

(22) PCT Filed: Sep. 17, 2019

(86) PCT No.: PCT/CN2019/106196
§ 371 (c)(1),
(2) Date: Mar. 10, 2021

(87) PCT Pub. No.: WO2020/057503
PCT Pub. Date: Mar. 26, 2020

(65) Prior Publication Data
US 2022/0031791 A1 Feb. 3, 2022

(30) Foreign Application Priority Data
Sep. 17, 2018 (CN) .......................... 201811080557.5

(51) Int. Cl.
| | | |
|---|---|---|
| *A61K 36/718* | (2006.01) | |
| *A61P 3/10* | (2006.01) | |
| *A61K 31/366* | (2006.01) | |
| *A61K 31/4375* | (2006.01) | |
| *A61K 31/7048* | (2006.01) | |
| *A61K 36/062* | (2006.01) | |
| *A61K 36/428* | (2006.01) | |
| *A61K 36/54* | (2006.01) | |
| *A61K 36/752* | (2006.01) | |
| *A61K 36/8888* | (2006.01) | |

(52) U.S. Cl.
CPC .......... *A61K 36/718* (2013.01); *A61K 31/366* (2013.01); *A61K 31/4375* (2013.01); *A61K 31/7048* (2013.01); *A61K 36/062* (2013.01); *A61K 36/428* (2013.01); *A61K 36/54* (2013.01); *A61K 36/752* (2013.01); *A61K 36/8888* (2013.01); *A61P 3/10* (2018.01)

(58) Field of Classification Search
None
See application file for complete search history.

(56) References Cited

FOREIGN PATENT DOCUMENTS

| CN | 102114076 A | * | 7/2011 |
| CN | 102423382 A | * | 4/2012 |
| CN | 107115431 A | * | 9/2017 |

OTHER PUBLICATIONS

Sham, T.T., et al., A Review on the Traditional Chinese Medicinal Herbs and Formulae with Hypolipidemic Effect, Review Article | BioMed Research International/Article , Open Access, vol. 2014 | Article ID 925302 | https://doi.org/10.1155/2014/925302).*
Machine translation of CN-107115431-A.*
Machine translation of CN-102423382-A.*
Machine translation of CN-102114076-A.*

* cited by examiner

*Primary Examiner* — H. Sarah Park
(74) *Attorney, Agent, or Firm* — Paratus Law Group, PLLC

(57) ABSTRACT

Disclosed are a traditional Chinese medicine composition and a traditional Chinese medicine extract composition for treating metabolic syndrome. The traditional Chinese medicine composition consists of the following raw materials in the following weight ratio: 5-80% of Coptidis Rhizoma, 5-70% of Aurantii Fructus Immaturus, 0-60% of Pinelliae Rhizoma, 0-40% of Trichosanthis Fructus, 0-12% of Cinnamomi Cortex, and 10-60% of red yeast rice. The traditional Chinese medicine extract composition consists of the following raw materials in the following weight ratio: 2-30% of Coptidis Rhizoma extract, and 70-98% of a mixed extract from five traditional Chinese medicines comprising Aurantii Fructus Immaturus, Pinelliae Rhizoma, red yeast rice, Trichosanthis Fructus, and Cinnamomi Cortex. The traditional Chinese medicine composition or the traditional Chinese medicine extract composition contains the following active ingredients (mg/g): 6-122 mg/g of total alkaloids, which comprises 4-89 mg/g of berberine, 30-315 mg/g of total flavonoids, which comprises 20-186 mg/g of neohesperidin: and 0.5-9 mg/g of lovastatin. Further provided are preparation methods and applications of the above compositions.

14 Claims, No Drawings

TRADITIONAL CHINESE MEDICINE COMPOSITION FOR TREATING METABOLIC SYNDROME AND PREPARATIONS THEREOF

CROSS REFERENCE TO PRIOR APPLICATION

This application is a National Stage Patent Application of PCT International Patent Application No. PCT/CN2019/106196 (filed on Sep. 17, 2019) under 35 U.S.C. § 371, which claims priority to Japanese Patent Application No. 201811080557.5 (filed on Sep. 17, 2018), which are all hereby incorporated by reference in their entirety.

TECHNICAL FIELD

The present invention relates to the field of medical technologies, in particular to a traditional Chinese medicine composition and preparations thereof.

BACKGROUND

Metabolic syndrome is a clinical syndrome that seriously affects human health. Main connotation of metabolic syndrome includes impaired glucose tolerance, hypertension, hyperlipidemia, and central obesity. Metabolic syndrome has insulin resistance as the common pathological basis and the clustering of a plurality of metabolic diseases as clinical characteristics. At present, one quarter to one third of adults in the world are affected by metabolic syndrome. As the population ages and overweight prevails, morbidity of this disease is increasing on a yearly basis. In the past 20 years, the morbidity of metabolic syndrome among American adults has risen from 21% to 39%. Among the adult population over the age of 20 in China, the morbidity of metabolic syndrome is 14%-18% by using the WHO standard and 12%-21% by using the NCEP-ATPIII standard. Patients with metabolic syndrome have 2-3 times higher morbidity and mortality during cardiovascular events and strokes than those without metabolic syndrome. The risk for non-diabetic patients with metabolic syndrome to develop type 2 diabetes is 5 times higher than those without metabolic syndrome. Among people with metabolic syndrome, around 45% have abnormal glucose metabolism, more than 80% have abnormal blood lipids, and around 90% have elevated blood pressure. At present, western treatment methods mainly involve combined application of a variety of drugs to control metabolic syndrome, which is expensive, inconvenient, and has relatively serious side effects. Neither there is any effective prescription in traditional Chinese medicine. Currently, there is still no international drug dedicated for treating metabolic syndrome due to the complexity of metabolic syndrome, so it is of great significance to carry out clinical research for new drugs dedicated for metabolic syndrome. The present invention will fill the gap in the international field.

BRIEF SUMMARY

An object of the present invention is to provide a traditional Chinese medicine composition, wherein the traditional Chinese medicine composition comprises Coptidis Rhizoma, Aurantii Fructus Immaturus, Pinelliae Rhizoma, Trichosanthis Fructus, Cinnamomi Cortex, and red yeast rice.

In the composition, Aurantii Fructus Immaturus is preferably Aurantii Fructus Immaturus parched with bran, Pinelliae Rhizoma is preferably Pinelliae Rhizoma Praeparatumcum Zingibere Et Alumine, and Trichosanthis Fructus is preferably whole Trichosanthis Fructus. Preferably, the composition comprises 5-80 wt % of Coptidis Rhizoma, 5-70 wt % of Aurantii Fructus Immaturus, 0-60 wt % of Pinelliae Rhizoma, 0-40 wt % of Trichosanthis Fructus, 2-12 wt % of Cinnamomi Cortex, and 10-60 wt % of red yeast rice. More preferably, the composition comprises 10-30 wt % of Coptidis Rhizoma, 10-30 wt % of Aurantii Fructus Immaturus, 10-30 wt % of Pinelliae Rhizoma, 5-30 wt % of Trichosanthis Fructus, 2-10 wt % of Cinnamomi Cortex, and 12-36 wt % of red yeast rice. Most preferably, a preferred ratio combination in the composition is as follows: 19.6 wt % of Coptidis Rhizoma, 19.6 wt % of Aurantii Fructus Immaturus, 19.6 wt % of Pinelliae Rhizoma, 26.1 wt % of Trichosanthis Fructus, 2.1 wt % of Cinnamomi Cortex, and 13.0 wt % of red yeast rice.

A second object of the present invention is to provide a traditional Chinese medicine composition, wherein the composition comprises Coptidis Rhizoma, Aurantii Fructus Immaturus, red yeast rice, and one or a plurality of optional selections from the group consisting of Pinelliae Rhizoma, Trichosanthis Fructus, and Cinnamomi Cortex. The one or plurality of selections comprise 1, 2, or 3 selections.

The composition comprises 5-80 wt % of Coptidis Rhizoma, 5-70 wt % of Aurantii Fructus Immaturus, 0-60 wt % of Pinelliae Rhizoma, 0-40 wt % of Trichosanthis Fructus, 0-12 wt % of Cinnamomi Cortex, and 10-60 wt % of red yeast rice.

The composition comprises 5-80 wt % of Coptidis Rhizoma, 5-70 wt % of Aurantii Fructus Immaturus, 0-60 wt % of Pinelliae Rhizoma, 5-40 wt % of Trichosanthis Fructus, 2-12 wt % of Cinnamomi Cortex, and 10-60 wt % of red yeast rice.

The composition comprises 5-80 wt % of Coptidis Rhizoma, 5-70 wt % of Aurantii Fructus Immaturus, 10-60 wt % of Pinelliae Rhizoma, 0-40 wt % of Trichosanthis Fructus, 2-12 wt % of Cinnamomi Cortex, and 10-60 wt % of red yeast rice.

The composition comprises 5-80 wt % of Coptidis Rhizoma, 5-70 wt % of Aurantii Fructus Immaturus, 10-60 wt % of Pinelliae Rhizoma, 5-40 wt % of Trichosanthis Fructus, 0-12 wt % of Cinnamomi Cortex, and 10-60 wt % of red yeast rice.

The composition comprises 5-80 wt % of Coptidis Rhizoma, 5-70 wt % of Aurantii Fructus Immaturus, 0-60 wt % of Pinelliae Rhizoma, 0-40 wt % of Trichosanthis Fructus, 2-12 wt % of Cinnamomi Cortex, and 10-60 wt % of red yeast rice.

The composition comprises 5-80 wt % of Coptidis Rhizoma, 5-70 wt % of Aurantii Fructus Immaturus, 0-60 wt % of Pinelliae Rhizoma, 5-40 wt % of Trichosanthis Fructus, 0-12 wt % of Cinnamomi Cortex, and 10-60 wt % of red yeast rice.

The composition comprises 5-80 wt % of Coptidis Rhizoma, 5-70 wt % of Aurantii Fructus Immaturus, 10-60 wt % of Pinelliae Rhizoma, 0-40 wt % of Trichosanthis Fructus, 0-12 wt % of Cinnamomi Cortex, and 10-60 wt % of red yeast rice.

Aurantii Fructus Immaturus is preferably Aurantii Fructus Immaturus parched with bran, Pinelliae Rhizoma is preferably Pinelliae Rhizoma Praeparatumcum Zingibere Et Alumine, and Trichosanthis Fructus is preferably whole Trichosanthis Fructus.

Another object of the present invention is to provide a traditional Chinese medicine extract composition, prepared by mixing extracts of the following six traditional Chinese medicinal materials consisting of: Coptidis Rhizoma, Aurantii Fructus Immaturus, Pinelliae Rhizoma, Trichosanthis Fructus, Cinnamomi Cortex, and red yeast rice. The content ratio of the extracts is as follows: a total alkaloids extract of Coptidis Rhizoma (hereinafter referred to Coptidis Rhizoma extract) accounts for 2-30%, and a mixed extract of five traditional Chinese medicinal materials consisting of Aurantii Fructus Immaturus, Pinelliae Rhizoma, red yeast rice (of the total amount in prescription, 10-100% of the red yeast rice is extracted, 0-90% is pulverized into fine powder as a disintegrant or filler, the same below), Trichosanthis Fructus, and Cinnamomi Cortex accounts for 70-98%. Preferably, the Coptidis Rhizoma extract accounts for 3-25%, and the mixed extract of five traditional Chinese medicinal materials consisting of Aurantii Fructus Immaturus, Pinelliae Rhizoma, red yeast rice, Trichosanthis Fructus, and Cinnamomi Cortex accounts for 75-97%. Most preferably, the Coptidis Rhizoma extract accounts for 5-15%, and the mixed extract of five traditional Chinese medicinal materials consisting of Aurantii Fructus Immaturus, Pinelliae Rhizoma, red yeast rice, Trichosanthis Fructus, and Cinnamomi Cortex accounts for 85-98%.

Red yeast rice fine powder (0-90% of the total prescription amount) and the Coptidis Rhizoma extract are well mixed with the mixed extract of the five traditional Chinese medicinal materials consisting of Aurantii Fructus Immaturus, Pinelliae Rhizoma, red yeast rice, Trichosanthis Fructus, and Cinnamomi Cortex, or with respective extracts of the above five traditional Chinese medicinal materials, to prepare the traditional Chinese medicine extract composition.

The traditional Chinese medicine extract composition contains the following active ingredients (mg/g): 6-122 mg/g of total alkaloids (the sum of berberine hydrochloride, jatrorrhizine hydrochloride, coptisine hydrochloride and palmatine hydrochloride, the same below), which comprise 4-89 mg/g of berberine; 30-315 mg/g of total flavonoids (the sum of three flavonoid glycosides consisting of neohesperidin, hesperidin, and naringin, the same below), which comprise 20-186 mg/g of neohesperidin; and 0.5-9 mg/g of lovastatin.

The traditional Chinese medicine extract composition contains the following active ingredients (mg/g): 12-122 mg/g of total alkaloids, which comprise 9-89 mg/g of berberine; 130-315 mg/g of total flavonoids, which comprise 80-186 mg/g of neohesperidin; and 1-9 mg/g of lovastatin.

The traditional Chinese medicine extract composition preferably contains the following active ingredients (mg/g): 20-85 mg/g of total alkaloids, which comprise 15-62 mg/g of berberine; 140-250 mg/g of total flavonoids, which comprise 90-170 mg/g of neohesperidin; and 1-5 mg/g of lovastatin.

The traditional Chinese medicine extract composition more preferably contains the following active ingredients (mg/g): 30-75 mg/g of total alkaloids, which comprise 20-50 mg/g of berberine; 110-250 mg/g of total flavonoids, which comprise 60-120 mg/g of neohesperidin; and 1-5 mg/g of lovastatin.

The traditional Chinese medicine extract composition preferably contains the following active ingredients (mg/g): 20-85 mg/g of total alkaloids, which comprise 15-62 mg/g of berberine; 100-250 mg/g of total flavonoids, which comprise 30-170 mg/g of neohesperidin; and 1-5 mg/g of lovastatin.

The traditional Chinese medicine extract composition more preferably contains the following active ingredients (mg/g): 30-75 mg/g of total alkaloids, which comprise 20-50 mg/g of berberine; 110-250 mg/g of total flavonoids, which comprise 40-120 mg/g of neohesperidin; and 1-5 mg/g of lovastatin.

Another object of the present invention is to provide a method for preparing a traditional Chinese medicine extract. Coptidis Rhizoma is extracted by using acid water, and filtration, concentration, alkali precipitation, salting-out, filtration, drying, pulverization are performed to prepare a total alkaloids extract. Four medicinal materials consisting of: red yeast rice (10-100% of the prescribed dosage), Aurantii Fructus Immaturus, Pinelliae Rhizoma, and Cinnamomi Cortex, are extracted by using 50-90% ethanol, and filtration is performed. Trichosanthis Fructus is extracted by using 75-95% ethanol, a Trichosanthis Fructus extraction solution is merged with an extraction solution of the four traditional Chinese medicinal materials, ethanol is recovered, decompression concentration, drying, and pulverization are performed to prepare a mixed extract of five traditional Chinese medicinal materials consisting of: Aurantii Fructus Immaturus, Pinelliae Rhizoma, red yeast rice, Cinnamomi Cortex, and Trichosanthis Fructus; or five traditional Chinese medicinal materials consisting of: red yeast rice, Aurantii Fructus Immaturus, Pinelliae Rhizoma, Cinnamomi Cortex, and Trichosanthis Fructus, are mixed and extracted by using 50-90% ethanol, filtration is performed, decompression is performed to recover ethanol, concentration, drying, and pulverization are performed to prepare a mixed extract of the five traditional Chinese medicinal materials consisting of: red yeast rice, Aurantii Fructus Immaturus, Pinelliae Rhizoma, Cinnamomi Cortex, and Trichosanthis Fructus; or red yeast rice, Aurantii Fructus Immaturus, Pinelliae Rhizoma, Cinnamomi Cortex, and Trichosanthis Fructus are separately extracted by using 50-90% ethanol, filtration is performed to separately prepare an ethanol extraction solution of the individual traditional Chinese medicinal material, the separately prepared ethanol extraction solutions of the five traditional Chinese medicinal materials are filtered separately, decompression is performed to recover ethanol, and concentration, drying, and pulverization are performed to prepare respective extracts of the five traditional Chinese medicinal materials consisting of: red yeast rice, Aurantii Fructus Immaturus, Pinelliae Rhizoma, Cinnamomi Cortex, and Trichosanthis Fructus. The respective extracts of the five traditional Chinese medicinal materials are mixed to prepare a mixed extract of the five traditional Chinese medicinal materials. The Coptidis Rhizoma extract and the mixed extract of the five traditional Chinese medicinal materials are mixed to prepare the traditional Chinese medicine extract composition.

In the composition, the Coptidis Rhizoma is extracted by using 0.1-1% sulfuric acid water, filtration is performed, a filtrate is concentrated, calcium hydroxide is added for alkali precipitation, a precipitate is removed, the pH value of the filtrate is regulated to an acid pH value by using hydrochloric acid, then sodium chloride is added to salt out the precipitate, and the precipitate is separated out, washed, filtered, dried, and pulverized, to prepare the Coptidis Rhizoma extract.

In the composition, four medicinal materials consisting of: red yeast rice (10-100% of the prescribed dosage), Aurantii Fructus Immaturus, Pinelliae Rhizoma, and Cinnamomi Cortex, are extracted by using 50-90% ethanol, and filtration is performed; and Trichosanthis Fructus is extracted by using 75-95% ethanol, a Trichosanthis Fructus extraction solution is merged with an extraction solution of the above four traditional Chinese medicinal materials, ethanol is recovered, decompression concentration, drying, and pulverization are performed to prepare a mixed extract of five traditional Chinese medicinal materials consisting of: Aurantii Fructus Immaturus, Pinelliae Rhizoma, red yeast rice, Cinnamomi Cortex, and Trichosanthis Fructus.

In the composition, five traditional Chinese medicinal materials consisting of: red yeast rice, Aurantii Fructus Immaturus, Pinelliae Rhizoma, Cinnamomi Cortex, and Trichosanthis Fructus, are mixed and extracted by using 50-90% ethanol, filtration is performed, decompression is performed to recover ethanol, concentration, drying, and pulverization are performed to prepare a mixed extract of the five traditional Chinese medicinal materials consisting of: red yeast rice, Aurantii Fructus Immaturus, Pinelliae Rhizoma, Cinnamomi Cortex, and Trichosanthis Fructus. Alternatively, red yeast rice, Aurantii Fructus Immaturus, Pinelliae Rhizoma, Cinnamomi Cortex, and Trichosanthis Fructus are separately extracted by using 50-90% ethanol, filtration is performed to separately prepare an ethanol extraction solution of the individual traditional Chinese medicinal material, the separately prepared ethanol extraction solutions of the five traditional Chinese medicinal materials are filtered separately, decompression is performed to recover ethanol, and concentration, drying, pulverization, and mixing are performed to prepare respective extracts of the five traditional Chinese medicinal materials consisting of: red yeast rice, Aurantii Fructus Immaturus, Pinelliae Rhizoma, Cinnamomi Cortex, and Trichosanthis Fructus. In the ethanol-extraction of the mixed extract or the respective extracts of the traditional Chinese medicinal materials consisting of: red yeast rice, Aurantii Fructus Immaturus, Pinelliae Rhizoma, Cinnamomi Cortex, and Trichosanthis Fructus, the ethanol is preferably 60-85% ethanol.

The mixed extract of the five traditional Chinese medicinal materials or the respective extracts of the five traditional Chinese medicinal materials, or the Trichosanthis Fructus extract and the extracts of four medicinal materials consisting of: Aurantii Fructus Immaturus, Pinelliae Rhizoma, red yeast rice, and Cinnamomi Cortex are mixed with the Coptidis Rhizoma extract and 0-90% red yeast rice fine powder which is used as a tablet disintegrant or a filler, to prepare the traditional Chinese medicine extract composition, Another object of the present invention is to provide a Chinese medicine composition and an administration dosage thereof.

A daily administration dosage of the traditional Chinese medicine composition of the present invention is as follows: 1.5-9 g of Coptidis Rhizoma, 1.5-9 g of Aurantii Fructus Immaturus, 0-12 g of Pinelliae Rhizoma, 0-12 g of Trichosanthis Fructus, 0-5 g of Cinnamomi Cortex, and 1.5-30 g of red yeast rice. A preferred dosage is 3-6 g of Coptidis Rhizoma, 3-6 g of Aurantii Fructus Immaturus, 3-6 g of Pinelliae Rhizoma, 0-6 g of Trichosanthis Fructus, 0.5-2.5 g of Cinnamomi Cortex, and 1.5-6 g of Red yeast rice. A more preferred dosage is 4.5 g of Coptidis Rhizoma, 4.5 g of Aurantii Fructus Immaturus, 4.5 g of Pinelliae Rhizoma, 6 g of Trichosanthis Fructus, 0.5 g of Cinnamomi Cortex, and 3 g of red yeast rice.

Another object of the present invention is to provide a traditional Chinese medicine extract composition and an administration dosage thereof.

An administration dosage of the traditional Chinese medicine extract composition of the present invention is 1-15 g per day, a preferred administration dosage is 2-10 g per day, and a more preferred administration dosage is 3-6 g per day.

The traditional Chinese medicine extract composition contains the following active ingredients (mg/g): 6-122 mg/g of total alkaloids, which comprise 4-89 mg/g of berberine; 30-315 mg/g of total flavonoids, which comprise 20-186 mg/g of neohesperidin; and 0.5-9 mg/g of lovastatin.

In some examples, the traditional Chinese medicine extract composition contains the following active ingredients (mg/g): 12-122 mg/g of total alkaloids, which comprise 9-89 mg/g of berberine; 130-315 mg/g of total flavonoids, which comprise 80-186 mg/g of neohesperidin; and 1-9 mg/g of lovastatin.

In some examples, the traditional Chinese medicine extract composition preferably contains the following active ingredients (mg/g): 20-85 mg/g of total alkaloids, which comprise 15-62 mg/g of berberine; 100-250 mg/g of total flavonoids, which comprise 30-170 mg/g of neohesperidin; and 1-5 mg/g of lovastatin. In some examples, the traditional Chinese medicine extract composition more preferably contains the following active ingredients (mg/g): 30-75 mg/g of total alkaloids, which comprise 20-50 mg/g of berberine; 110-250 mg/g of total flavonoids, which comprise 40-120 mg/g of neohesperidin; and 1-5 mg/g of lovastatin.

In some examples, the traditional Chinese medicine extract composition preferably contains the following active ingredients (mg/g): 20-85 mg/g of total alkaloids, which comprise 15-62 mg/g of berberine; 140-250 mg/g of total flavonoids, which comprise 90-170 mg/g of neohesperidin; and 1-5 mg/g of lovastatin. In some examples, the traditional Chinese medicine extract composition more preferably contains the following active ingredients (mg/g): 30-75 mg/g of total alkaloids, which comprise 20-50 mg/g of berberine; 110-250 mg/g of total flavonoids, which comprise 60-120 mg/g of neohesperidin; and 1-5 mg/g of lovastatin.

DETAILED DESCRIPTION

Modern Research Review

Coptidis Rhizoma: The main components of Coptidis Rhizoma are berberine hydrochloride, jatrorrhizine hydrochloride, coptisine hydrochloride, palmatine hydrochloride, etc. Coptidis Rhizoma has functions such as reducing blood glucose, reducing serum lipid, antioxidation, antibacteria, and antivirus.

Aurantii Fructus Immaturus: The main components of Aurantii Fructus Immaturus are flavonoids and alkaloids. The main effective components of Aurantii Fructus Immaturus are naringin, hesperidin, neohesperidin and synephrine. Aurantii Fructus Immaturus has functions such as improving gastrointestinal functions, anti-thrombosis, and strengthening myocardial contraction.

Trichosanthis Fructus: The main effective components of Trichosanthis Fructus are flavonoids and saponins. Trichosanthis Fructus has functions such as anti-expectoration, antibacteria, myocardial ischemia prevention, and anti-aging.

Pinelliae Rhizoma: The main effective components of Pinelliae Rhizoma are 6-gingerol and alkaloids, etc. Pinelliae Rhizoma has functions such as anti-hypotension and anti-tussis.

Cinnamomi Cortex: The main components of Cinnamomi Cortex are cinnamic acid and cinnamaldehyde. Cinnamomi Cortex has functions such as depression and anti-hypotension.

Red yeast rice: The main effective component of red yeast rice is lovastatin. Red yeast rice has the functions of lowering blood lipids, enhancing non-specific immunity, increasing the phagocytic rate of phagocytes, increasing the production of antibodies, and improving the function of T cells.

Analysis of Prescription:

Metabolic syndrome is caused by eating greasy and delicious delicacies, phlegm converted to heat and blocking in Middle-Jiao. Coptidis Rhizoma in the prescription is bitter in flavor, cold in nature and enters the heart, stomach, large intestine meridians. It has the functions of eliminating heat and purging fire, regulating stomach and removing abdominal distention and accumulated mass, clearing away stomach heat and relieving thirst. As mentioned in the book of Yao Lei Fa Xiang, "(Coptidis Rhizoma has the function of) Clearing the heart fire, removing damp heat of the spleen and stomach, and is able to cure irritability, nausea, heat stagnation in the Middle-Jiao, and vomiting. It is a necessary herb to treat epigastric fullness". The epigastric fullness means the symptom of "epigastric distention, press which will cause pain" described in Zhongjing Xiaoxianxiong Decoction, which is similar to the abdominal distension symptom of metabolic syndrome. Therefore, Coptidis Rhizoma is considered monarch medicine.

Pinelliae Rhizoma Praeparatumcum Zingibere Et Alumine is pungent-warm in property and enters the spleen, stomach and lung meridians. It has the functions of resolving phlegm to dispersing nodule, dispelling phlegm and eliminating stagnation of the stomach, reducing reversed qi and relieving vomiting. Pinelliae Rhizoma is described in Ming Yi Bie Lu as "Eliminating phlegm and heat in the chest and hypochondrium, coughing, epigastric distention, vomiting". When Pinelliae Rhizoma and Coptidis Rhizoma are used together, one pungent and one bitter, pungent-opening and bitter-descending, both of them enter Middle-Jiao, clear heat and eliminate phlegm, disperse stagnation and resolve accumulated mass. Trichosanthis Fructus are bitter-cold in nature and enters the lung and stomach meridians. It has the functions of clearing away heat and removing phlegm, removing rheumatic pain and opening collaterals, promoting qi and moistening the intestine. Patients with metabolic syndrome have a firm and distended abdomen, only Trichosanthis Fructus wilt can remove the distention. The compatibility of Pinelliae Rhizoma and Trichosanthis Fructus can moisturize dryness, clear heat and eliminate phlegm. The compatibility of Trichosanthis Fructus and Coptidis Rhizoma can go for Middle-Jiao, bitter but not dry, bitter to discend and melting phlegm in Middle-Jiao. The combination of these three medicines comes from "Xiao Xian Xiong Decoction". Aurantii Fructus Immaturus fried with bran is bitter-cold in nature and flavor and entered the lung, stomach meridians. It has the functions of promoting abdominal Qi and eliminating phlegm in body. Aurantii Fructus Immaturus is described in Ming Yi Bie Lu as "Eliminating phlegm in the chest and hypochondrium, relieving fluid retention, dissipating stagnant qi and relieving distension, epigastric distention, pain and reversing qi". In Yao Pin Hua Yi, "(Aurantii Fructus Immaturus) promotes digestion and mitigating the stomach, resolve the nodule, promoting the blood, relieving distension, expelling phlegm, removing fluid retention, removing undigested food and relieving constipation". Patients with metabolic syndrome have a firm and distended abdomen, Only Aurantii Fructus Immaturus wilt can disperse. Therefore, Pinelliae Rhizoma Praeparatumcum Zingibere Et Alumine, Trichosanthis Fructus, Aurantii Fructus Immaturus all act as Minister medicine. The bitter of Coptidis Rhizoma are reducing, the pungent of Pinelliae Rhizoma to diffuse, the bitter of Trichosanthis Fructus is to moisturize the large intestine, the bitter of Aurantii Fructus Immaturus to promote flow of stagnant qi. As Jiegu Zhang said, "To cure the epigastric distention and indigestion, use Aurantii Fructus Immaturus combined with Coptidis Rhizoma".

Red yeast rice is sweet-warm in nature and non-toxic. It enters liver, spleen, stomach and large intestine meridians. It has the functions of promoting digestion and mitigating the stomach, and is good at eliminating fat and turbidity, promoting blood circulation and dissolving blood stasis. It is described in Ben Cao Yan Yi Bu Yi "(Red yeast rice has the function of) promoting blood flow and food digest, strengthening spleen and warming the stomach". In Ben Cao Qiu Yuan, "Red yeast rice is made from Japonica rice meal by adding wine koji to turn it red. It has the effect of promoting blood circulation by flow of nutritive qi, and also have the function of warming the stomach and promoting digestion. It can treat Qi stagnation and blood stasis caused by emotional stagnation". Therefore, Red yeast rice acts as assistant medicine in the prescription.

Cinnamomi Cortex is pungent-warm in nature and has the functions of dispersing qi stagnation in the Middle-Jiao Cinnamomi Cortex is described in Yu Qiu Yao Jie as "Cinnamomi Cortex can warm stomach and tonify the warm qi in blood. With fragrant and sweet flavor acting on spleen, pungent and sweet flavor acting on liver, pungent and fragrant flavor can relieve stagnations, and is best in regulating qi stagnation in liver and spleen". When Cinnamomi Cortex and Coptidis Rhizoma are used together, one pungent and one bitter, pungent-opening and bitter-descending, purging heat and protecting spleen, cold compatible with heat nature medicine, they can prevent the possible unfavorable effect brought to middle-jiao caused by bitter and cold nature of Coptidis Rhizoma, but can also disperse the nodules and promote fluid production. Therefore, Cinnamomi Cortex acts as guide medicine in the prescription.

With these herbs compatible with each other in the whole prescription, it has the effects of clearing heat, eliminating phlegm, and promoting qi circulation to relieve distension. It is used to treat symptoms caused by the stagnation of phlegm-heat, such as obesity, enlarged abdomen, chest distress, excessive phlegm, inappetence and feeling of fullness in stomach and abdomen, dry mouth, thirst, polydipsia, and easy hunger, irritability, flushing and oily face, snoring at night, loose or dry stool, yellow urine, red tongue with yellow coating and slippery pulse. It can also treat patients with hyperlipidemia, diabetes, hypertension, obesity, metabolic syndrome (abdominal obesity with blood sugar, glycosylated hemoglobin, blood pressure, blood lipids and uric acid abnormalities) in Western medicine. The efficacy test was conducted in KKAy mice with spontaneous type 2 diabetes characterized by insulin resistance and obesity and C57BL/6J mice fed with high-fat diet as experimental animal models. 500, 1000, and 1500 mg/kg (equivalent to adults taking 3000 mg, 6000 mg, and 9000 mg of the traditional Chinese medicine extract composition of the present invention) were given respectively to investigate the effects of the traditional Chinese medicine composition of the present invention on the related indexes of metabolic syndrome such as insulin resistance, glycolipid metabolism and blood pressure. The results indicate that the traditional Chinese medicine composition of the present invention has the following effects: (1) reducing blood glucose; (2) lowering blood insulin level; (3) improving oral glucose tolerance abnormality; (4) reducing glycosylated hemoglobin (HbA1c); (5) increasing insulin sensitivity index and improving insulin resistance; and (6) reducing the level of blood triglyceride, having a tendency to reduce total cholesterol and reduce blood pressure. Therefore, the preferred daily administration dosage of the traditional Chinese medicine extract composition of the present invention is set to about 2-10 g.

The drug stability research test indicates that the tablet of the Chinese medicine composition of the present invention is easy to absorb moisture and is more sensitive to high humidity than high temperature and light, high temperature has obvious influence on the content of cinnamaldehyde, and light has a significant effect on the content of lovastatin. Under a final packaging condition, the coated tablet is packaged with an aluminum-plastic blister as the inner packaging, and an aluminum foil bag as the outer packaging. An accelerated test was carried out at temperature of 40° C.±2° C. and relative humidity of 75%±5% for 6 months. The rate of change in weight after moisture absorption of the traditional Chinese medicine composition tablet of the present invention is within 0.5%, indicating that the packaging condition offers a good moisture-proof effect. The amounts of berberine hydrochloride, total alkaloids of Coptidis Rhizoma, total flavonoids of Citrus aurantium, and naringin of Citrus aurantium in the Chinese medicine composition tablet of the present invention change very slightly; the amount of lovastatin changes slightly, with a change rate within 12.23%, and the change is mainly caused by the interconversion of isomers and does not affect the efficacy.

The tablet of the traditional Chinese medicine composition of the present invention is determined via the stability study as: having an aluminum-plastic blister package as the inner packaging and being stored in a sealed condition at a dry place. Under the above storage condition, the finished product is stable, a moisture proofing effect is good, and an effective period is tentatively set to two years.

One of the objects of the present invention is to provide a Chinese medicine composition, which has definite effective ingredients, mechanism of action, definite pharmacological activity and clinical efficacy, has controllable quality, and is safe for administration.

The technical solution adopted in the present invention is as follows: a traditional Chinese medicine composition comprises Coptidis Rhizoma, Aurantii Fructus Immaturus, Pinelliae Rhizoma, Trichosanthis Fructus, Cinnamomi Cortex, and red yeast rice.

In the composition, Aurantii Fructus Immaturus is preferably Aurantii Fructus Immaturus parched with bran, Pinelliae Rhizoma is preferably Pinelliae Rhizoma Praeparatumcum Zingibere Et Alumine, and Trichosanthis Fructus is preferably whole Trichosanthis Fructus.

Preferably, the composition includes 5-80 wt % of Coptidis Rhizoma, 5-70 wt % of Aurantii Fructus Immaturus, 0-60 wt % of Pinelliae Rhizoma, 0-40 wt % of Trichosanthis Fructus, 2-12 wt % of Cinnamomi Cortex, and 10-60 wt % of red yeast rice. More preferably, the composition includes 10-30 wt % of Coptidis Rhizoma, 10-30 wt % of Aurantii Fructus Immaturus, 10-30 wt % of Pinelliae Rhizoma, 5-30 wt % of Trichosanthis Fructus, 2-10 wt % of Cinnamomi Cortex, and 12-36 wt % of red yeast rice. Most preferably, a preferred ratio combination in the composition is as follows: 19.6 wt % of Coptidis Rhizoma, 19.6 wt % of Aurantii Fructus Immaturus, 19.6 wt % of Pinelliae Rhizoma, 26.1 wt % of Trichosanthis Fructus, 2.1 wt % of Cinnamomi Cortex, and 13.0 wt % of red yeast rice.

The present invention provides another technical solution: the composition includes Coptidis Rhizoma, Aurantii Fructus Immaturus, red yeast rice, and one or a plurality of optional selections from the group consisting of Pinelliae Rhizoma, Trichosanthis Fructus, and Cinnamomi Cortex.

The composition includes 5-80 wt % of Coptidis Rhizoma, 5-70 wt % of Aurantii Fructus Immaturus, 0-60 wt % of Pinelliae Rhizoma, 0-40 wt % of Trichosanthis Fructus, 0-12 wt % of Cinnamomi Cortex, and 10-60 wt % of red yeast rice.

An administration dosage of the traditional Chinese medicine composition is 10-50 g per day, a preferred administration dosage is 14-38 g per day, and a more preferred administration dosage is 18-25 g per day.

In another aspect, the present invention provides a traditional Chinese medicine extract composition, prepared by mixing extracts of the following six traditional Chinese medicinal materials: Coptidis Rhizoma, Aurantii Fructus Immaturus, Pinelliae Rhizoma, Trichosanthis Fructus, Cinnamomi Cortex, and red yeast rice. The content ratio of the extracts is as follows: a Coptidis Rhizoma extract accounts for 2-30%, and a mixed extract of five traditional Chinese medicinal materials consisting of Aurantii Fructus Immaturus, Pinelliae Rhizoma, red yeast rice (of which 10-100% thereof is extracted, 0-90% thereof is pulverized into fine powder as a disintegrant or filler, the same below), Trichosanthis Fructus, and Cinnamomi Cortex accounts for 70-98%. Preferably, the Coptidis Rhizoma extract accounts for 3-25%, and the mixed extract of five traditional Chinese medicinal materials consisting of Aurantii Fructus Immaturus, Pinelliae Rhizoma, red yeast rice, Trichosanthis Fructus, and Cinnamomi Cortex accounts for 75-97%. More preferably, the Coptidis Rhizoma extract accounts for 5-15%, and the mixed extract of five traditional Chinese medicinal materials consisting of Aurantii Fructus Immaturus, Pinelliae Rhizoma, red yeast rice, Trichosanthis Fructus, and Cinnamomi Cortex accounts for 85-95%.

The traditional Chinese medicine extract composition contains the following active ingredients (mg/g): 6-122 mg/g of total alkaloids, which comprise 4-89 mg/g of berberine; 30-315 mg/g of total flavonoids, which comprise 20-186 mg/g of neohesperidin; and 0.5-9 mg/g of lovastatin. Preferably, the traditional Chinese medicine extract composition contains the following active ingredients (mg/g): 20-85 mg/g of total alkaloids, which comprise 15-62 mg/g of berberine; 100-250 mg/g of total flavonoids, which comprise 30-170 mg/g of neohesperidin; and 1-5 mg/g of lovastatin. More preferably, the traditional Chinese medicine extract composition contains the following active ingredients (mg/g): 30-75 mg/g of total alkaloids, which comprise 20-50 mg/g of berberine; 110-250 mg/g of total flavonoids, which comprise 40-120 mg/g of neohesperidin; and 1-5 mg/g of lovastatin.

The traditional Chinese medicine extract composition contains the following active ingredients (mg/g): 12-122 mg/g of total alkaloids, which comprise 9-89 mg/g of berberine; 130-315 mg/g of total flavonoids, which comprise 80-186 mg/g of neohesperidin; and 1-9 mg/g of lovastatin. Preferably, the traditional Chinese medicine extract composition contains the following active ingredients (mg/g): 20-85 mg/g of total alkaloids, which comprise 15-62 mg/g of berberine; 140-250 mg/g of total flavonoids, which comprise 90-170 mg/g of neohesperidin; and 1-5 mg/g of lovastatin. More preferably, the traditional Chinese medicine extract composition contains the following active ingredients (mg/g): 30-75 mg/g of total alkaloids, which comprise 20-50 mg/g of berberine; 110-250 mg/g of total flavonoids, which comprise 60-120 mg/g of neohesperidin; and 1-5 mg/g of lovastatin.

An administration dosage of the Chinese medicine extract composition is 1-15 g per day, a preferred administration dosage is 2-10 g per day, and a more preferred administration dosage is 3-6 g per day.

The Chinese medicine composition and Chinese medicine extract composition can be prepared into pharmaceutical preparations, such as injections, tablets, capsules, granules, and oral liquids.

The Chinese medicine composition and Chinese medicine extract composition have the effects of clearing heat, dissipating phlegm, and promoting qi circulation to relieve distension. The compositions are used to treat symptoms caused by the stagnation of phlegm-heat, such as body fat, enlarged abdomen, chest tightness, excessive phlegm, inappetence and feeling of fullness in stomach and abdomen, dry mouth, thirst, polydipsia, and easy hunger, irritable, flushing and oily face, snoring at night, loose or dry stool, yellow urine, red tongue with thin yellow coating, slippery pulse. The compositions can also treat symptoms of hyperlipidemia, diabetes, hypertension, obesity, metabolic syndrome (abdominal obesity with blood sugar, glycosylated hemoglobin, blood pressure, blood lipids and uric acid abnormalities) in Western medical system.

The Chinese medicine composition and Chinese medicine extract composition can be used to prepare medicines for treating one or a plurality of the following: metabolic syndrome, obesity, high blood sugar, high blood pressure, and high cholesterol.

In some examples, the medicines are used for treating one or a plurality of the following: disorder of blood glucose and lipid metabolism, obesity, hyperglycemia, hypertension, and hyperlipidemia, in the early stage of metabolic syndrome. In some examples, the medicines are used for one or a plurality of the following: reducing blood glucose, reducing the hypoglycemic insulin level, improving oral glucose tolerance abnormality, reducing the glycated hemoglobin (HbA1c) level, increasing the insulin sensitivity index, improving insulin resistance, reducing the blood triglyceride level, reducing total cholesterol, and reducing blood pressure.

The plurality includes the number of 2, 3, 4, 5, 6, 7, 8, and 9.

The traditional Chinese medicine extract composition of the present invention has the following beneficial technical effects.

(1) Significant improvement to the metabolic syndrome.

Pharmacodynamic comparison test results of the extracts prepared according to embodiments 1-7 indicate that the extracts of the present invention have statistically different effects on reducing blood sugar, serum triglycerides, and total cholesterol. Systematic pharmacodynamic studies have proven that the traditional Chinese medicine extract composition of the present invention has the following effects: reducing body weight, lowering blood sugar, lowering blood insulin levels, improving oral glucose tolerance abnormality, reducing glycosylated hemoglobin (HbA1c), increasing insulin sensitivity indexes, improving insulin resistance, reducing the level of blood triglyceride, reducing total cholesterol, and reducing blood pressure.

(2) Stable Properties and Controllable Quality of the Traditional Chinese Medicine Composition of the Present Invention The tablet of the traditional Chinese medicine composition of the present invention is determined via the stability study as: having an aluminum-plastic blister package as the inner packaging and being stored in a sealed condition at a dry place. Under the above storage condition, the finished product is stable, a moisture proofing effect is good, and an effective period is tentatively set to two years.

(3) Safe Use of the Traditional Chinese Medicine Composition of the Present Invention Regarding the traditional Chinese medicine composition of the present invention, in an oral administration-based acute toxicity test on mice, it is detected that $LD_{50}$ is greater than 20000 mg/kg, which is 200 times the clinically planned dosage. In an oral administration-based acute toxicity test on Beagle dogs, it is detected that a lethal dosage is more than 7500 mg/kg, which is 75 times the clinically planned dosage.

In an administration-based chronic toxicity test on rats, dosages of the traditional Chinese medicine composition of the present invention are 8, 28, and 98 times of the clinically planned dosage, and results prove that a clinically planned dosage of the traditional Chinese medicine composition of the present invention is safe.

(4) Applicability of the traditional Chinese medicine composition of the present invention to industrial production. After 9 batches of pilot production, the process is feasible.

DETAILED DESCRIPTION OF EMBODIMENTS

The following embodiments are used to illustrate the present invention, but not to limit the scope of the present invention. If the specific technology or conditions are not specified in the embodiments, it shall be carried out in accordance with the technology or conditions described in the literature in the field, or in accordance with the product instruction. Those reagents or instruments with manufacturers not specified are all conventional products that can be purchased through formal channels.

Example 1

Prescription 1: 1.5 g (7.9 wt %) of Coptidis Rhizoma, 6 g (31.6 wt %) of Aurantii Fructus Immaturus, 3 g (15.8 wt %) of Pinelliae Rhizoma, 0 g (0 wt %) of Trichosanthis Fructus, 2.5 g (13.1 wt %) of Cinnamomi Cortex, and 6 g (31.6 wt %) of red yeast rice, with a total daily administration dosage of 19 g. The amount of prepared extracts is 5.58 g, with a yield of 29.4%.

Preparation method: Coptidis Rhizoma was pulverized into coarse powder or cut into medicinal slices in a suitable size and placed into an extraction tank, 0.5% sulfuric acid of 10 times of the amount was added, extraction was performed three times by means of heating decoction, with each time lasting 2 h, filtration was performed, extraction solutions were merged, decompression was performed for concentration, a concentrated solution was placed into a precipitation tank and stirred, lime milk was added slowly to regulate the pH value to 9, the solution was maintained to stand, filtration was performed to remove a calcium sulfate precipitate, the pH value of a filtrate was regulated to 1-2 by using concentrated hydrochloric acid, sodium chloride was added to 10% of the amount, salting-out was performed, the solution was maintained to stand for 24 h, suction filtration was performed, a precipitate was washed with water until the pH value reaches 5, and decompression was performed for drying at 60° C., to obtain a total alkaloids extract.

The following medicinal materials: Aurantii Fructus Immaturus parched with bran, Pinelliae Rhizoma Praeparatumcum Zingibere Et Alumine, red yeast rice, and Cinnamomi Cortex, were pulverized into coarse powder or cut into medicinal slices in a suitable size, the medicinal materials were prepared according to prescribed dosages, mixed, and placed into an ethanol reflux extraction tank, 70% ethanol of 10 times of the amount and 70% ethanol of 8 times of the amount were respectively added for extraction for two times, with each time lasting 1 hour, filtration was performed, decompression was performed to recover ethanol, concentration and drying were performed to obtain a mixed extract of the four traditional Chinese medicinal materials.

The four traditional Chinese medicinal materials consisting of Aurantii Fructus Immaturus, Pinelliae Rhizoma, Cinnamomi Cortex, and red yeast rice were well mixed with the Coptidis Rhizoma extract to obtain the final traditional Chinese medicine extract composition of the present invention.

Content detection results (mg/g): the total alkaloids content is 12.53 mg/g (including 9.27 mg/g of berberine), the total flavonoids content is 292.48 mg/g (including 171.11 mg/g of neohesperidin); and the lovastatin content is 4.31 mg/g.

Example 2

Prescription 2: 4.5 g (45 wt %) of Coptidis Rhizoma, 3 g (30 wt %) of Aurantii Fructus Immaturus, 0 g (0 wt %) of Pinelliae Rhizoma, 0.5 g (5 wt %) of Trichosanthis Fructus, 0.5 g (5 wt %) of Cinnamomi Cortex, and 1.5 g (15 wt %) of red yeast rice, with a total daily administration dosage of 10 g. The amount of prepared extracts is 2.74 g, with a yield of 27.4%.

Preparation method: a total alkaloids extract of Coptidis Rhizoma was prepared by means of the method in Example 1.

The following medicinal materials: Aurantii Fructus Immaturus parched with bran, red yeast rice, Trichosanthis Fructus, and Cinnamomi Cortex, were prepared according to prescribed dosages, mixed, and placed into an ethanol reflux extraction tank, 70% ethanol of 10 times of the amount and 70% ethanol of 8 times of the amount were respectively added for extraction for two times, with each time lasting 1 hour, filtration was performed, decompression was performed to recover ethanol, concentration and drying were performed to obtain a mixed extract of the four traditional Chinese medicinal materials.

The four traditional Chinese medicinal materials consisting of Aurantii Fructus Immaturus, red yeast rice, Trichosanthis Fructus, and Cinnamomi Cortex were well mixed with the Coptidis Rhizoma extract to obtain the traditional Chinese medicine extract composition of the present invention.

Content detection results (mg/g): the total alkaloids content is 85.34 mg/g (including 62.24 mg/g of berberine), the total flavonoids content is 290.358 mg/g (including 170.37 mg/g of neohesperidin); and the lovastatin content is 2.03 mg/g.

Example 3

Prescription 3: 4.5 g (21.4 wt %) of Coptidis Rhizoma, 4.5 g (21.4 wt %) of Aurantii Fructus Immaturus, 0 g (0 wt %) of Pinelliae Rhizoma, 0 g (0 wt %) of Trichosanthis Fructus, 0 g (0 wt %) of Cinnamomi Cortex, and 12 g (57.2 wt %) of red yeast rice, with a total daily administration dosage of 21 g. The amount of prepared extracts is 5.21 g, with a yield of 24.8%.

Preparation method: a total alkaloids extract of Coptidis Rhizoma was prepared by means of the method in Example 1.

A mixed extract of two traditional Chinese medicinal materials consisting of Aurantii Fructus Immaturus parched with bran and red yeast rice was prepared by means of the method in Example 1.

The mixed extract of the two traditional Chinese medicinal materials consisting of Aurantii Fructus Immaturus and red yeast rice was well mixed with the Coptidis Rhizoma extract to obtain the traditional Chinese medicine extract composition of the present invention.

Content detection results (mg/g): the total alkaloids content is 43.51 mg/g (including 31.83 mg/g of berberine), the total flavonoids content is 234.38 mg/g (including 136.56 mg/g of neohesperidin); and the lovastatin content is 9.31 mg/g.

Example 4

Prescription 4: 4.5 g (32.1 wt %) of Coptidis Rhizoma, 4.5 g (32.1 wt %) of Aurantii Fructus Immaturus, 0 g (0 wt %) of Pinelliae Rhizoma, 0 g (0 wt %) of Trichosanthis Fructus, 0.5 g (3.6 wt %) of Cinnamomi Cortex, and 4.5 g (32.1 wt %) of red yeast rice, with a total daily administration dosage of 14 g. The amount of prepared extracts is 374 g, with a yield of 26.7%.

Preparation method: a total alkaloids extract of Coptidis Rhizoma was prepared by means of the method in Example 1.

A mixed extract of three traditional Chinese medicinal materials consisting of Aurantii Fructus Immaturus parched with bran, red yeast rice, and Cinnamomi Cortex was prepared by means of the method in Example 1.

The mixed extract of the three traditional Chinese medicinal materials consisting of Aurantii Fructus Immaturus parched with bran, red yeast rice, and Cinnamomi Cortex was well mixed with the Coptidis Rhizoma extract to obtain the traditional Chinese medicine extract composition of the present invention.

Content detection results (mg/g): the total alkaloids content is 63.42 mg/g (including 46.25 mg/g of berberine), the total flavonoids content is 315.19 mg/g (including 185.75 mg/g of neohesperidin); and the lovastatin content is 4.63 mg/g.

Example 5

Prescription 5: 6 g (33.8 wt %) of Coptidis Rhizoma, 1.5 g (8.5 wt %) of Aurantii Fructus Immaturus, 6 g (33.8 wt %) of Pinelliae Rhizoma, 0 g (0 wt %) of Trichosanthis Fructus, 1.25 g (7 wt %) of Cinnamomi Cortex, and 3 g (16.9 wt %) of red yeast rice, with a total daily administration dosage of 17.75 g. The amount of prepared extracts is 2.64 g, with a yield of 14.9%.

Preparation method: a total alkaloids extract of Coptidis Rhizoma was prepared by means of the method in Example 1.

A mixed extract of four traditional Chinese medicinal materials consisting of Aurantii Fructus Immaturus parched with bran, Pinelliae Rhizoma, red yeast rice, and Cinnamomi Cortex was prepared by means of the method in Example 1.

The mixed extract of the four traditional Chinese medicinal materials consisting of Aurantii Fructus Immaturus parched with bran, Pinelliae Rhizoma, red yeast rice, and Cinnamomi Cortex was well mixed with the Coptidis Rhizoma extract to obtain the traditional Chinese medicine extract composition of the present invention.

Content detection results (mg/g): the total alkaloids content is 122.06 mg/g (including 89.03 mg/g of berberine), the total flavonoids content is 161.34 mg/g (including 92.86 mg/g of neohesperidin); and the lovastatin content is 4.87 mg/g.

Example 6

Prescription 6: 4.5 g (19.57 wt %) of Coptidis Rhizoma, 4.5 g (19.56 wt %) of Aurantii Fructus Immaturus, 4.5 g (19.57 wt %) of Pinelliae Rhizoma, 6 g (26.09 wt %) of Trichosanthis Fructus, 0.5 g (2.17 wt %) of Cinnamomi Cortex, and 3 g (13.04 wt %) of red yeast rice, with a total daily administration dosage of 23 g. The amount of prepared extracts is 4.4 g, with a yield of 19.1%.

Preparation method: a total alkaloids extract of Coptidis Rhizoma was prepared by means of the method in Example 1.

90% of the total prescription amount of red yeast rice, Aurantii Fructus Immaturus parched with bran, Pinelliae Rhizoma, and Cinnamomi Cortex were pulverized into coarse powder or cut into medicinal slices in a suitable size and prepared according to prescribed dosages, mixed, and placed into an ethanol reflux extraction tank, 70% ethanol of 10 times of the amount and 70% ethanol of 8 times of the amount were respectively added for extraction for two times, with each time lasting 1 hour, a solution was maintained to stand, and then filtration was performed; 85% ethanol of 7 times of the amount and 85% ethanol of 5 times of the amount were respectively added to the Trichosanthis Fructus medicinal material or medicinal slices for extraction for two times, with each time lasting 1 hour, a solution was maintained to stand, and then filtration was performed, the solution was merged with the ethanol extraction solution of the four traditional Chinese medicinal materials, ethanol was recovered, and decompression concentration, drying, pulverization were performed to a mixed extract of the five traditional Chinese medicinal materials.

The Coptidis Rhizoma extract, the mixed extract of the five traditional Chinese medicinal materials, and 10% of the prescribed dosage of red yeast rice fine powder which is used as a tablet disintegrant or a filler, were well mixed to obtain the traditional Chinese medicine extract composition of the present invention.

Content detection results (mg/g): the total alkaloids content is 47.05 mg/g (including 31.58 mg/g of berberine), the total flavonoids content is 203.6 mg/g (including 108.3 mg/g of neohesperidin); and the lovastatin content is 2.59 mg/g.

Example 7

Prescription 7: 4.5 g (19.57 wt %) of Coptidis Rhizoma, 4.5 g (19.56 wt %) of Aurantii Fructus Immaturus, 4.5 g (19.57 wt %) of Pinelliae Rhizoma, 6 g (26.09 wt %) of Trichosanthis Fructus, 0.5 g (2.17 wt %) of Cinnamomi Cortex, and 3 g (13.04 wt %) of red yeast rice, with a total daily administration dosage of 23 g. The amount of prepared extracts is 5.62 g, with a yield of 24.4%.

Preparation method: a total alkaloids extract of Coptidis Rhizoma was prepared by means of the method in Example 1.

Aurantii Fructus Immaturus parched with bran was pulverized into coarse powder or cut into medicinal slices in a suitable size, prepared according to the prescribed dosage, and placed into an ethanol reflux extraction tank, 70% ethanol of 8 times of the amount was added for extraction for two times, with each time lasting 1 hour, filtration was performed, decompression was performed to recover ethanol, and concentration and drying were performed to obtain an extract of Aurantii Fructus Immaturus parched with bran.

Pinelliae Rhizoma Praeparatumcum Zingibere Et Alumine was pulverized into coarse powder or cut into medicinal slices in a suitable size, prepared according to the prescribed dosage, and placed into an ethanol reflux extraction tank, 70% ethanol of 8 times of the amount was added for extraction for two times, with each time lasting 1 hour, filtration was performed, decompression was performed to recover ethanol, and concentration and drying were performed to obtain an extract of Pinelliae Rhizoma Praeparatumcum Zingibere Et Alumine.

Medicinal slices of whole Trichosanthis Fructus were prepared according to the prescribed dosage and placed into an ethanol reflux extraction tank, 70% ethanol of 8 times of the amount was added for extraction for two times, with each time lasting 1 hour, filtration was performed, decompression was performed to recover ethanol, and concentration and drying were performed to obtain an extract of whole Trichosanthis Fructus.

Red yeast rice was prepared according to the prescribed dosage and placed into an ethanol reflux extraction tank, 70% ethanol of 8 times of the amount was added for extraction for two times, with each time lasting 1 hour, filtration was performed, decompression was performed to recover ethanol, and concentration and drying were performed to obtain an extract of red yeast rice.

Cinnamomi Cortex was prepared according to the prescribed dosage and placed into an ethanol reflux extraction tank, 70% ethanol of 8 times of the amount was added for extraction for two times, with each time lasting 1 hour, filtration was performed, decompression was performed to recover ethanol, and concentration and drying were performed to obtain an extract of Cinnamomi Cortex.

Aurantii Fructus Immaturus, Cinnamomi Cortex, Pinelliae Rhizoma, Trichosanthis Fructus, and red yeast rice were well mixed to obtain a mixed extract of the five traditional Chinese medicinal materials. The mixed extract of the five traditional Chinese medicinal materials was well mixed with the Coptidis Rhizoma extract to obtain the traditional Chinese medicine extract composition of the present invention.

Content detection results (mg/g): the total alkaloids content is 38.69 mg/g (including 28.10 mg/g of berberine), the total flavonoids content is 204.49 mg/g (including 123.2 mg/g of neohesperidin); and the lovastatin content is 2.27 mg/g.

Comparative Example 1

Prescription: 0 g (0 wt %) of Coptidis Rhizoma, 4.5 g (24.32 wt %) of Aurantii Fructus Immaturus, 4.5 g (24.32 wt %) of Pinelliae Rhizoma, 6 g (32.43 wt %) of Trichosanthis Fructus, 0.5 g (2.70 wt %) of Cinnamomi Cortex, and 3 g (16.21 wt %) of red yeast rice, with a total daily administration dosage of 18.5 g. The amount of prepared extracts is 5.9 g, with a yield of 31.9%.

Preparation method: preparation was performed according to the extraction method of the corresponding ingredients in Example 6.

Content detection results (mg/g): the total alkaloids content is 0 mg/g (including 0 mg/g of berberine), the total flavonoids content is 34.16 mg/g (including 20.11 mg/g of neohesperidin); and the lovastatin content is 0.14 mg/g.

Comparative Example 2

Prescription: 4.5 g (24.32 wt %) of Coptidis Rhizoma, 0 g (0 wt %) of Aurantii Fructus Immaturus, 4.5 g (24.32 wt %) of Pinelliae Rhizoma, 6 g (32.43 wt %) of Trichosanthis Fructus, 0.5 g (2.70 wt %) of Cinnamomi Cortex, and 3 g (16.21 wt %) of red yeast rice, with a total daily administration dosage of 18.5 g. The amount of prepared extracts is 4.06 g, with a yield of 21.9%.

Preparation method: preparation was performed according to the extraction method of the corresponding ingredients in Example 6.

Content detection results (mg/g): the total alkaloids content is 9.53 mg/g (including 6.98 mg/g of berberine), the total flavonoids content is 0 mg/g (including 0 mg/g of neohesperidin); and the lovastatin content is 0.55 mg/g.

Comparative Example 3

Prescription: 4.5 g (22.5 wt %) of Coptidis Rhizoma, 4.5 g (22.5 wt %) of Aurantii Fructus Immaturus, 4.5 g (22.5 wt %) of Pinelliae Rhizoma, 6 g (30 wt %) of Trichosanthis Fructus, 0.5 g (2.5 wt %) of Cinnamomi Cortex, and 0 g (0 wt %) of red yeast rice, with a total daily administration dosage of 20 g. The amount of prepared extracts is 5.71 g, with a yield of 28.55%.

Preparation method: preparation was performed according to the extraction method of the corresponding ingredients in Example 6.

Content detection results (mg/g): the total alkaloids content is 6.88 mg/g (including 4.96 mg/g of berberine), the total flavonoids content is 36.01 mg/g (including 21.67 mg/g of neohesperidin); and the lovastatin content is 0 mg/g.

Comparative Example 4

Prescription: 4.5 g (50 wt %) of Coptidis Rhizoma, 4.5 g (50 wt %) of Aurantii Fructus Immaturus, 0 g (0 wt %) of Pinelliae Rhizoma, 0 g (0 wt %) of Trichosanthis Fructus, 0 g (0 wt %) of Cinnamomi Cortex, and 0 g (0 wt %) of red yeast rice, with a total daily administration dosage of 9 g. The amount of prepared extracts is 2.66 g, with a yield of 9.56%.

Preparation method: preparation was performed according to the extraction method of the corresponding ingredients in Example 6.

Content detection results (mg/g): the total alkaloids content is 15.11 mg/g (including 10.65 mg/g of berberine), the total flavonoids content is 76.71 mg/g (including 46.62 mg/g of neohesperidin); and the lovastatin content is 0 mg/g.

Comparative Example 5

Prescription: 4.5 g (29.03 wt %) of Coptidis Rhizoma, 0 g (0 wt %) of Aurantii Fructus Immaturus, 4.5 g (29.03 wt %) of Pinelliae Rhizoma, 6 g (38.71 wt %) of Trichosanthis Fructus, 0.5 g (3.22 wt %) of Cinnamomi Cortex, and 0 g (0 wt %) of red yeast rice, with a total daily administration dosage of 15.5 g. The amount of prepared extracts is 3.46 g, with a yield of 22.32%.

Preparation method: preparation was performed according to the extraction method of the corresponding ingredients in Example 6.

Content detection results (mg/g): the total alkaloids content is 11.88 mg/g (including 8.12 mg/g of berberine), the total flavonoids content is 0 mg/g (including 0 mg/g of neohesperidin); and the lovastatin content is 0 mg/g.

Drug prescriptions and active ingredient content detection results in Examples 1-7 and Comparative examples 1-5 are summarized as follows:

TABLE I

| | | Coptidis Rhizoma | Aurantii Fructus Immaturus | Pinelliae Rhizoma | Trichosanthis Fructus | Cinnamomi Cortex | Red yeast rice | Total prescription dosage |
|---|---|---|---|---|---|---|---|---|
| Example 1 | Weight (g) | 1.5 | 6 | 3 | 0 | 2.5 | 6 | 19 |
| | Proportion (%) | 7.89 | 31.57 | 15.79 | 0 | 13.16 | 31.57 | |
| Example 2 | Weight (g) | 4.5 | 3 | 0 | 0.5 | 0.5 | 1.5 | 10 |
| | Proportion (%) | 45 | 30 | 0 | 5 | 5 | 15 | |
| Example 3 | Weight (g) | 4.5 | 4.5 | 0 | 0 | 0 | 12 | 21 |
| | Proportion (%) | 21.4 | 21.4 | 0 | 0 | 0 | 57.2 | |
| Example 4 | Weight (g) | 4.5 | 4.5 | 0 | 0 | 0.5 | 4.5 | 14 |
| | Proportion (%) | 32.1 | 32.1 | 0 | 0 | 3.57 | 32.1 | |
| Example 5 | Weight (g) | 6 | 1.5 | 6 | 0 | 1.25 | 3 | 17.75 |
| | Proportion (%) | 33.8 | 8.5 | 33.8 | 0 | 7 | 16.9 | |
| Example 6 | Weight (g) | 4.5 | 4.5 | 4.5 | 6 | 0.5 | 3 | 23 |
| | Proportion (%) | 19.57 | 19.57 | 19.57 | 26.1 | 2.17 | 13.04 | |
| Example 7 | Weight (g) | 4.5 | 4.5 | 4.5 | 6 | 0.5 | 3 | 23 |
| | Proportion (%) | 19.57 | 19.57 | 19.57 | 26.1 | 2.17 | 13.04 | |
| Weight range | | 1.5-6 | 1.5-6 | 0-6 | 0-6 | 0-2.5 | 1.5-12 | |
| Optimal prescription (Example 6) | | 4.5 | 4.5 | 4.5 | 6 | 0.5 | 3 | Daily Dose |
| Comparative example 1 | Weight (g) | 0 | 4.5 | 4.5 | 6 | 0.5 | 3 | 18.5 |
| | Proportion (%) | 0 | 24.32 | 24.32 | 32.43 | 2.7 | 16.21 | |
| Comparative example 2 | Weight (g) | 4.5 | 0 | 4.5 | 6 | 0.5 | 3 | 18.5 |
| | Proportion (%) | 24.32 | 0 | 24.32 | 32.43 | 2.7 | 16.21 | |

TABLE I-continued

Drug prescriptions

|  |  | Coptidis Rhizoma | Aurantii Fructus Immaturus | Pinelliae Rhizoma | Trichosanthis Fructus | Cinnamomi Cortex | Red yeast rice | Total prescription dosage |
|---|---|---|---|---|---|---|---|---|
| Comparative example 3 | Weight (g) | 4.5 | 4.5 | 4.5 | 6 | 0.5 | 0 | 20 |
|  | Proportion (%) | 22.5 | 22.5 | 22.5 | 30 | 2.5 | 0 |  |
| Comparative example 4 | Weight (g) | 4.5 | 4.5 | 0 | 0 | 0 | 0 | 9 |
|  | Proportion (%) | 50 | 50 | 0 | 0 | 0 | 0 |  |
| Comparative example 5 | Weight (g) | 4.5 | 0 | 4.5 | 6 | 0.5 | 0 | 15.5 |
|  | Proportion (%) | 29.03 | 0 | 29.03 | 38.71 | 3.22 | 0 |  |

TABLE II

Content detection results (mg/g)

|  | Total alkaloids | Berberine | Total flavonoids | Neohesperidin | Lovastatin |
|---|---|---|---|---|---|
| Example 1 | 12.53 | 9.27 | 292.48 | 171.11 | 4.31 |
| Example 2 | 85.34 | 62.24 | 290.35 | 170.37 | 2.03 |
| Example 3 | 43.51 | 31.83 | 234.38 | 136.56 | 9.31 |
| Example 4 | 63.42 | 46.25 | 315.19 | 185.75 | 4.63 |
| Example 5 | 122.06 | 89.03 | 161.34 | 92.86 | 4.87 |
| Example 6 | 47.05 | 31.58 | 203.6 | 108.3 | 2.59 |
| Example 7 | 38.69 | 28.10 | 204.49 | 123.2 | 2.27 |
| Comparative example 1 | 0 | 0 | 34.16 | 20.11 | 0.41 |
| Comparative example 2 | 9.53 | 6.98 | 0 | 0 | 0.55 |
| Comparative example 3 | 6.88 | 4.96 | 36.01 | 21.67 | 0 |
| Comparative example 4 | 15.11 | 10.65 | 76.71 | 46.62 | 0 |
| Comparative example 5 | 11.88 | 8.12 | 0 | 0 | 0 |

Example 8

Prescription 8: The extract mixture prepared according to Example 6.

TABLE III

| Preparation prescription | Dosage/1000 tablets (g) | Proportion (%) |
|---|---|---|
| Traditional Chinese medicine extract composition | 1010 | 92.9 |
| Red yeast rice powder | 75 | 6.9 |
| Magnesium stearate | 1.1 | 0.1 |
| Silicon dioxide | 1.1 | 0.1 |
| Film coating premixed agent | 20-25 | Weight gain of 2-2.5 |

Preparation method: extraction powder was weighed according to the prescription dosage and added into a dry granulator for granulation and sieving, magnesium stearate and silicon dioxide were added, a mixture was well mixed and pressed into tablets by using a special punch. Each tablet weighs 1.1 g, and 1000 tablets are prepared. The qualified tablets are coated with dark reddish-brown moisture-proof film coating, and a weight gain is 2-2.5%. The tablets were packaged to obtain a final product. Administration method: 2-5 tablets each time, and 2-3 times a day.

TABLE IV

Test results of three batches of pilot products

| Project | 20170301 | 20170302 | 20170303 |
|---|---|---|---|
| Character | Up to specification | Up to specification | Up to specification |
| Weight variation | Up to specification | Up to specification | Up to specification |
| Disintegration time | 20 min | 23 min | 21 min |
| Berberine hydrochloride (mg/tablet) | 31.4 | 35.5 | 34.7 |
| Total amount of four alkaloids (mg/tablet) | 45.1 | 50.3 | 48.0 |
| Lovastatin (mg/tablet) | 4.6 | 4.0 | 4.4 |
| Neohesperidin (mg/tablet) | 100.8 | 102.3 | 99.8 |
| Total flavonoids (mg/tablet) | 158.2 | 170.7 | 156.6 |

Example 9

Prescription 9: The extract mixture prepared according to Example 5.

TABLE V

| Preparation prescription | Dosage/1000 tablets (g) | Proportion (%) |
|---|---|---|
| Traditional Chinese medicine extract composition | 798.4 | 99.8 |
| Microcrystalline cellulose | 0 | 0 |
| Magnesium stearate | 0.8 | 0.1 |
| Silicon dioxide | 0.8 | 0.1 |
| Film coating premixed agent | 20-25 | Weight gain of 2-2.5 |

The preparation method is the same as that in Example 8, wherein each tablet weighs 0.8 g.

Administration method: 1-2 tablets each time, and 3 times a day.

TABLE VI

Test results of three batches of pilot products

| Project | 20160401 | 20160402 | 20160403 |
|---|---|---|---|
| Character | Up to specification | Up to specification | Up to specification |

TABLE VI-continued

Test results of three batches of pilot products

| Project | 20160401 | 20160402 | 20160403 |
|---|---|---|---|
| Weight variation | Up to specification | Up to specification | Up to specification |
| Disintegration time | 19 min | 22 min | 23 min |
| Berberine hydrochloride (mg/tablet) | 60.3 | 57.4 | 58.8 |
| Total amount of four alkaloids (mg/tablet) | 95.6 | 90.7 | 91.5 |
| Lovastatin (mg/tablet) | 3.9 | 4.1 | 4.0 |
| Neohesperidin (mg/tablet) | 74.3 | 80.2 | 83.7 |
| Total flavonoids (mg/tablet) | 129.1 | 139.5 | 142.4 |

Example 10

Prescription 10: The extract mixture prepared according to Example 2.

TABLE VII

| Preparation prescription | Dosage/1000 capsules (g) | Proportion (%) |
|---|---|---|
| Traditional Chinese medicine extract composition | 450 | 90 |
| Calcium carbonate | 50 | 10 |

Preparation method: 50 g of calcium carbonate was added to 450 g of the extract mixture of six traditional Chinese medicinal materials, 95% ethanol was used as a binder to prepare a soft material, and the soft material was dried in an oven at 40° C. and encapsulated, to prepare 1000 capsules in total.

Administration method: 2-3 capsules each time, and 3 times a day.

TABLE VIII

Test results of three batches of pilot products

| Project | 20160401 | 20160402 | 20160403 |
|---|---|---|---|
| Character | Up to specification | Up to specification | Up to specification |
| Weight variation | Up to specification | Up to specification | Up to specification |
| Disintegration time | 8 min | 8 min | 7 min |
| Berberine hydrochloride (mg/capsule) | 28.2 | 27.2 | 29.3 |
| Total amount of four alkaloids (mg/capsule) | 38.7 | 38.1 | 39.6 |
| Lovastatin (mg/capsule) | 0.92 | 0.90 | 0.86 |
| Neohesperidin (mg/capsule) | 78.6 | 78.0 | 77.7 |
| Total flavonoids (mg/capsule) | 132.3 | 131.9 | 130.1 |

Example 11

Prescription 11: The extract mixture prepared according to Example 7.

TABLE IX

| Preparation prescription | Dosage (g)/1000 tablets |
|---|---|
| Traditional Chinese medicine extract composition | 2000 g |
| Mannitol | 2000 g |
| Aspartame | 100 g |
| 95% Ethanol | Appropriate amount |

Preparation method: the extract mixture was prepared according to the prescribed amount and then the mixed; extract powder was weighed according to the prescribed amount, mannitol and aspartame were added, a mixture was well mixed and added into a dry granulator for granulation and sieving, and granules were packaged. Each bag contains 4.1 g of the granules, and each bag contains 2 g of the extract.

Administration method: 1-2 bags each time, and 2-3 times a day.

TABLE X

Test results of three batches of pilot products

| Project | 20160401 | 20160402 | 20160403 |
|---|---|---|---|
| Character | Up to specification | Up to specification | Up to specification |
| Weight variation | Up to specification | Up to specification | Up to specification |
| Berberine hydrochloride (mg/bag) | 51.5 | 55.7 | 59.5 |
| Total amount of four alkaloids (mg/bag) | 79.8 | 76.1 | 81.2 |
| Lovastatin (mg/bag) | 4.5 | 3.9 | 4.9 |
| Neohesperidin (mg/bag) | 235.3 | 243.0 | 246.2 |
| Total flavonoids (mg/bag) | 379.3 | 402.3 | 410.7 |

I. Study on the Stability of the Traditional Chinese Medicine Composition of the Present Invention Sample source: the traditional Chinese medicine extract composition of the present invention is the extract prepared according to Example 8.

The stability study indicates that the tablet of the Chinese medicine composition of the present invention is easy to absorb moisture and is more sensitive to high humidity than high temperature and light, and light has a significant effect on the content of lovastatin. Under a final packaging condition, the coated tablet is packaged with an aluminum-plastic blister as the inner packaging, and an aluminum foil bag as the outer packaging. An accelerated test was carried out at temperature of 40° C.±2° C. and relative humidity of 75%±5% for 6 months. The rate of change in weight after moisture absorption of the traditional Chinese medicine composition tablet of the present invention was within 0.5%, indicating that the packaging condition offers a good moisture-proof effect. The amounts of berberine hydrochloride, total alkaloids of Coptidis Rhizoma, total flavonoids of Citrus aurantium, and naringin of Citrus aurantium in the Chinese medicine composition tablet of the present invention change very slightly; the amount of lovastatin changes slightly, with a change rate within 12.23%, and the change is mainly caused by the interconversion of isomers and does not affect the efficacy.

The tablet of the traditional Chinese medicine composition of the present invention is determined via the stability study as: having an aluminum-plastic blister package as the inner packaging, having an aluminum-plastic composite film bag as the outer packaging, and being stored in a sealed condition at a dry place, with an effective period tentatively set to two years.

TABLE XI

| Project | | Standard requirements | 0 month | 3 months | 6 months | 9 months | 12 months |
|---|---|---|---|---|---|---|---|
| Character | | The tablet should be a film-coated tablet, and the non-coated tablet is dark brown, slightly fragrant, and bitter | Up to specification | Up to specification | Up to specification | Up to specification | Up to specification |
| Identification | | (1) Pinelliae Rhizoma should comply with regulations | Up to specification | Up to specification | Up to specification | Up to specification | Up to specification |
| | | (2) Red yeast rice should comply with regulations | Up to specification | Up to specification | Up to specification | Up to specification | Up to specification |
| | | (3) Trichosanthis Fructus should comply with regulations | Up to specification | Up to specification | Up to specification | Up to specification | Up to specification |
| | | (4) Cinnamomi Cortex should comply with regulations | Up to specification | Up to specification | Up to specification | Up to specification | Up to specification |
| Test | Disintegration time | The tablet should be completely dissolved within 60 minutes | 23 min | 25 min | 24 min | 26 min | 26 min |
| | Weight variation | The tablet should comply with regulations | Up to specification | — | — | — | — |
| | Microbial limitation | The total number of aerobic bacteria shall not exceed $10^5$ cfu/g, the total number of molds and yeasts shall not exceed $5 \times 10^2$ cfu/g, and *Escherichia coli* (1 g) shall not be detected; *Salmonella* (10 g) shall not be detected; and the number of bile-salt-resistant gram-negative bacteria should be less than $10^2$ cfu/g. | Up to specification | — | — | — | — |
| Content determination | Alkaloids | Berberine hydrochloride content in each tablet should be 25-55 mg | 31.4 | 31.3 | 31.4 | 31.5 | 31.4 |
| | | Jatrorrhizine hydrochloride content in each tablet should be 2-6 mg | 3.1 | 3.2 | 3.2 | 3.1 | 3.2 |
| | | Coptisine hydrochloride content in each tablet should be 5-12 mg | 7.7 | 7.5 | 7.4 | 7.6 | 7.6 |
| | | Palmatine hydrochloride content in each tablet should be 2-8 mg | 2.9 | 2.8 | 2.8 | 2.9 | 2.8 |
| | | The total amount of four alkaloids in each tablet should be 40-75 mg | 45.1 | 44.8 | 44.8 | 45.1 | 45.0 |
| | Lovastatin | Lovastatin content in each tablet should be 2-5 mg | 4.6 | 4.6 | 4.5 | 4.4 | 4.5 |
| | flavonoids | neohesperidin content in each tablet should be 60-120 mg | 100.8 | 100.9 | 100.2 | 101.4 | 100.9 |
| | | Total amount of Naringin, hesperidin and neohesperidin in each tablet should be 110-250 mg | 158.3 | 158.5 | 158.1 | 159.3 | 158.9 |

Note:
— indicates that no detection is required.

II. Study on Prescription Screening of the Traditional Chinese Medicine Extract Composition of the Present Invention
1. Animals for tests: Wistar rats were purchased from Beijing Vital River Laboratory Animal Technology Co., Ltd. License number: SCXK (Beijing) 2016-0011.
2. Test Method
2.1 Preparation Method of an Animal Model for Glucose and Lipid Metabolism Disorder
2.1.1 High Fat Diet+Lipid Emulsion Gavage Causes Lipid Metabolism Disorder and Insulin Resistance 160 male Wistar rats (weighing 150-180 g) were provided by Beijing Vital River Laboratory Animal Center. After a week of adaptive feeding, the rats were randomly divided into a normal group and a high fat group. 20 rats in the normal group were fed with a conventional diet. 140 rats in the high fat group were fed with a high-fat diet, and the high fat group underwent gavage with lipid emulsion (1 ml/100 g weight/day) each day for 4 weeks.

After 4 weeks of feeding in the normal group and high fat group, blood was collected from the orbit to measure blood lipids. Compared with a normal group, the weight, serum triglycerides, and cholesterol of the rats in the high fat group increased significantly, indicating a disorder of lipid metabolism.

After an euglycemic clamp test, it is found that the high fat group has significantly lower glucose infusion rate (GIR) than the normal group, indicating that the insulin sensitivity of the rats in the high fat group was significantly decreased, and the animals had obvious insulin resistance.

2.1.2 Intraperitoneal Injection of Small Doses of STZ Causes Glucose Metabolism Disorders Preparation of a 1% Streptozocin (STZ) solution: a 0.1 mol/L sodium citrate buffer solution (pH 4.2) was added to 1.00 g of accurately weighed streptozotocin until the volume of a mixed solution reaches 100 mL, and the mixed solution was mixed well to obtain the 1% Streptozocin (STZ) solution. The preparation was performed before use.

The animals in the high fat group fasted for 24 hours, but water intake was permitted. 30 mg/kg/time of the newly prepared 1% streptozotocin sodium citrate solution was injected intraperitoneally. The normal group was intraperitoneally injected with an equal volume of a 0.1 mol/L sodium citrate buffer solution.

2.2 Blood Lipid Measurement Method

After 4 weeks of continuous high-fat feeding, 2 rats in each cage were randomly selected from each group. 0.2 mL of blood was collected from the orbit of the rats, collected in EP tubes, and centrifuged immediately after coagulation. Serum was collected and stored at −20° C. The serum was analyzed according to the method of the Plylai kit.

2.3 Euglycemic Clamp Test Method

After 4 weeks of continuous high-fat feeding, one rat was randomly select from each cage of the normal group (4 cages in total), wherein two rats were selected from the 4th cage; and one rat was randomly selected from each of the 4th, 9th, 14th, 19th, and 24th cage of the high fat group (28 cages in total), to perform the clamp test.

2.4 Preparation Method of a Drug Prescription

Example preparation method: the Chinese medicine extract composition of Examples 1-7 were respectively prepared according to the methods described in Examples 1-7. Comparative Example preparation method: the traditional Chinese medicine extract composition of Comparative examples 1-5 were respectively prepared according to the method described in Example 6.

2.5 Method of Administration

Model group and normal group: the rats underwent gavage with 0.5 mL/100 g weight/day of normal saline.

The dosage of the Chinese medicine extract composition in Examples 1-7 and Comparative examples 1-5 used in the rat test: 0.7 g/kg weight/day. Calculated by equivalent dosage method, the rat dosage is equivalent to a human dosage of 0.11 g/kg weight/day, equivalent to approximately 20-30 g of crude drug for each person (based on 60 kg weight) per day. The dosage of other prescription groups is calculated in the same proportion.

Preparation method of a gavage test sample: 10.00 g of weighed sodium carboxymethyl cellulose was added into 1000 mL of pure water and swelled, to obtain a 1% CMC-Na aqueous solution. The weighed extracts of different prescriptions were dispersed in the 1% CMC-Na aqueous solution, and a mixed solution was stirred and mixed well. The drug was prepared once a week and stored in a refrigerator at 4° C. Gavage administration was performed according to the following grouping solution.

TABLE 1

| Group | Total crude drug dosage (g) | Total extract dosage (g) | Extract dosage (g) | 1% CMC-Na (mL) |
|---|---|---|---|---|
| Prescription1 | 1266.6 | 374.1 | 14.0 | 100 |
| Prescription2 | 666.6 | 213.1 | 8.0 | 100 |
| Prescription3 | 1400 | 347.8 | 13.0 | 100 |
| Prescription4 | 933.3 | 249.5 | 9.3 | 100 |
| Prescription5 | 1183.33 | 176.5 | 6.6 | 100 |
| Prescription6 | 1533.3 | 266.4 | 9.9 | 100 |
| Prescription7 | 1533.3 | 396.5 | 14.8 | 100 |

Based on the grouping solution, gavage administration was performed at 8:30-10:30 every forenoon, with the dosage of 0.5 mL/100 g weight/day. After 4 weeks of continuous administration, the test rats fasted overnight for 12 hours, and the fasting blood glucose was measured by using a blood glucose meter (or measured by using blood glucose test strips). Subsequently, the rats were executed by bleeding from the femoral artery, blood samples were collected, serum was separated out, and five indicators of blood lipids were measured respectively. The individual weight change situation was recorded during the test.

2.6 Analysis Method for Statistical Data

All the data was entered into an Excel form to calculate an average and a standard deviation. Data of each group was represented by mean±SD. Data differences between the groups were analyzed using SPSS 11.5 software. First the homogeneity test of variance is performed, and then variance analysis was performed for each group.

3 Pharmacodynamic Test Results of Examples 3.1 Results of Blood Lipid Measurement after 4 Weeks of High-Fat Feeding After 4 weeks of feeding in the normal group and the high fat group (high-fat diet+lipid emulsion), 2 rats were randomly selected from each cage and blood was collected from the orbit to measure blood lipids. The results are shown in Table 2.

TABLE 2

| Group | Results of blood lipid test (mean ± SD) | | |
|---|---|---|---|
| | Triglycerides (mM) | Free cholesterol (μM) | Total cholesterol (μM) |
| Normal group | 0.971 ± 0.20 | 34.83 ± 11.01 | 101.06 ± 24.98 |
| High fat group | 1.313 ± 0.30** | 224.9 ± 63.4*** | 479.05 ± 138.02*** |

(Compared with normal group*$P < 0.001$, $P < 0.01$, *$P < 0.05$)

As shown in Table 2, after 4 weeks of feeding with high-fat diet and gavage with lipid emulsion, the blood lipids of the high-fat group increased significantly, significantly differing from those of the normal group. It is indicated that a lipid metabolism disorder model was successfully established.

3.2 Euglycemic Clamp Test Results

The results of the hyperinsulinemic-euglycemic clamp test are shown in Table 3.

TABLE 3

Results of the hyperinsulinemic-euglycemic clamp test on each group (mean ± SD)

| Group | Number (N) | Steady state glucose (mmol/L) | Glucose infusion rate (mg · kg$^{-1}$ · min$^{-1}$) |
|---|---|---|---|
| Normal group | 5 | 5.17 ± 0.31 | 21.24 ± 1.05 |
| High fat group | 5 | 5.43 ± 0.24 | 14.19 ± 0.96*** |

As shown in Table 3, after 4 weeks of feeding with high-fat diet and gavage with lipid emulsion, the glucose infusion rate and the insulin sensitivity of the rats in the high fat group were significantly decreased, and the animals showed obvious insulin resistance.

3.3 Grouping Results 3 days after the STZ injection, blood was collected from the tail vein to measure the fasting blood glucose (12 h fasting). Rats with blood glucose values higher than 26.6 mmol/L and lower than 13.3 mmol/L were excluded, and rats with blood glucose values between 13.3-26.6 mmol/L were selected and grouped. The grouped animals were classified into 4 levels according to the level of blood glucose, which were respectively 13.3-16.6 mmol/L level, 16.7-19.9 mmol/L level, 20.0-23.3 mmol/L level, and 23.4-26.6 mmol/L level Animals in each level were randomly divided into 8 groups according to the weights thereof. The grouping results are shown in Table 4. The 8 groups consisted of prescription group 1 to prescription group 7, and a model group.

TABLE 4

Fasting blood glucose and weights of rats in each group (mean ± SD)

| Group | Number of animals | Blood glucose (nmol/L) | Weight (g) |
|---|---|---|---|
| Control group | 12 | 4.94 ± 0.34 | 358.8 ± 12.1 |
| Prescription group 1 | 13 | 20.12 ± 3.41 | 372.3 ± 14.5 |
| Prescription group 2 | 14 | 19.25 ± 3.81 | 367.1 ± 17.5 |
| Prescription group 3 | 14 | 19.12 ± 3.99 | 366.1 ± 13.5 |
| Prescription group 4 | 13 | 19.33 ± 3.66 | 369.6 ± 18.5 |
| Prescription group 5 | 13 | 19.28 ± 3.87 | 367.7 ± 17.9 |
| Prescription group 6 | 14 | 19.32 ± 3.30 | 371.1 ± 16.4 |
| Prescription group 7 | 14 | 19.89 ± 3.29 | 365.7 ± 16.9 |
| Model group | 13 | 20.49 ± 3.61 | 362.7 ± 18.1 |

As shown in Table 4, the weights of the animals were evenly distributed in the model group and different groups, and there was no significant difference in the weight and blood glucose between the groups, indicating that the grouping was even.

The control group consisted of totally 12 normal rats without being modeled, weighing 358.75±12.08 g, and fasting blood glucose being 4.94±0.34. The control group has significant differences compared to the groups after modeling.

3.4 General Situation of Each Group

The rats in the normal control group have good mental condition, quick response, free movement, and shiny fur. The rats in the model group were lethargic, slow in response, and slow in movement after injected with STZ. After 4 weeks of treatment in each treatment group, the general situations were improved to different degrees.

3.5 Blood Glucose Change Situations in Each Group after Treatment

Grouping was performed according to Table 4. After 4 weeks of continuous administration, the test rats fasted overnight for 12 hours, and fasting blood glucose was measured (measured by using blood glucose meter+blood glucose test strip). The results are shown in Table 5.

TABLE 5

Fasting blood glucose values of each group after administration

| Group | Number of animals | Blood glucose (nmol/L) |
|---|---|---|
| Control group | 12 | 5.03 ± 0.30 |
| Prescription group 1 | 11 | 18.07 ± 2.74 |
| Prescription group 2 | 13 | 17.23 ± 4.10 |
| Prescription group 3 | 13 | 16.57 ± 3.77* |
| Prescription group 4 | 12 | 16.22 ± 3.56* |
| Prescription group 5 | 12 | 18.03 ± 4.05 |
| Prescription group 6 | 13 | 15.26 ± 3.56** |
| Prescription group 7 | 13 | 15.77 ± 3.52* |
| Model group | 11 | 19.65 ± 3.66 |

(Compared with model group*$P < 0.001$, $P < 0.01$, *$P < 0.05$)

Note: In the grouping according to Table 5, the prescription groups 1-7 respectively represent Examples 1-7 of the present invention, the same below.

As shown in Table 5, the fasting blood glucose values of the prescription groups 3, 4, 6, and 7 were significantly decreased compared with that in the model group, wherein the effect on the prescription group 6 was strongest.

3.6 Blood Lipid Change Situation of Each Group

After the blood glucose was measured, the animals in each group were executed by bleeding from the femoral artery, blood samples were collected, serum was separated out, and five indicators of blood lipids were respectively measured according to the above method. The results are shown in Table 6 and Table 7.

TABLE 6

Blood lipid values (mean ± SD) of each group measured after treatment

| Group | Triglycerides (μmol/L) | Free cholesterol (μmol/L) | Total cholesterol (μmol/L) |
|---|---|---|---|
| Control group | 643.58 ± 123.64*** | 68.62 ± 14.22*** | 130.99 ± 28.84*** |
| Prescription group 1 | 881.02 ± 265.24 | 133.42 ± 26.25** | 255.89 ± 70.85** |
| Prescription group 2 | 916.08 ± 226.25 | 152.32 ± 27.46 | 305.36 ± 53.7 |
| Prescription group 3 | 851.15 ± 190.33 | 130.56 ± 24.67** | 249.48 ± 58.32** |

TABLE 6-continued

Blood lipid values (mean ± SD) of each group measured after treatment

| Group | Triglycerides (μmol/L) | Free cholesterol (μmol/L) | Total cholesterol (μmol/L) |
|---|---|---|---|
| Prescription group 4 | 865.44 ± 238.45 | 136.79 ± 26.68* | 261.91 ± 59.23* |
| Prescription group 5 | 823.95 ± 273.67* | 142.63 ± 27.06 | 273.73 ± 58.98* |
| Prescription group 6 | 783.44 ± 223.13* | 137.40 ± 27.59* | 261.22 ± 61.17* |
| Prescription group 7 | 820.07 ± 217.42* | 137.58 ± 29.98* | 268.00 ± 53.10* |
| Model group | 1012.86 ± 208.78 | 163.27 ± 32.71 | 321.53 ± 62.08 |

(Compared with model group*$P < 0.001$, $P < 0.01$, *$P < 0.05$)

TABLE 7

Blood lipid values (mean ± SD) of each group measured after treatment

| Group | High density lipoprotein (μmol/L) | Low densith lipoprotein (μmol/L) |
|---|---|---|
| Control group | 684.13 ± 137.94* | 832.70 ± 162.49** |
| Prescription group 1 | 645.89 ± 141.38 | 945.63 ± 209.38 |
| Prescription group 2 | 586.08 ± 155.94 | 1034.84 ± 311.39 |
| Prescription group 3 | 660.81 ± 115.70 | 863.15 ± 242.26** |
| Prescription group 4 | 642.86 ± 179.26 | 994.80 ± 244.39 |
| Prescription group 5 | 634.92 ± 152.67 | 982.86 ± 260.33 |
| Prescription group 6 | 638.83 ± 140.53 | 910.40 ± 231.60* |
| Prescription group 7 | 631.50 ± 126.79 | 952.93 ± 225.64 |
| Model group | 547.19 ± 127.52 | 1126.19 ± 219.58 |

(Compared with model group*$P < 0.001$, $P < 0.01$, *$P < 0.05$)

As shown in Table 6 and Table 7, the 5 indicators of blood lipids of each of the prescription groups significantly differ from those of the model group. The triglyceride of each of the prescription groups 5, 6, and 7 significantly differs from that of the model group. The free cholesterol of each of prescription groups 1, 3, 4, 6, and 7 significantly differs from that of the model group. The total cholesterol of each of the prescription groups 1, 3, 4, 5, 6, and 7 significantly differs from that of the model group. By analysis in combination with the prescription and dosage of each prescription group, it is found that the increase in the dosage of red yeast rice has obvious effect on reducing cholesterol, but has no obvious effect on reducing triglyceride; each prescription group has a certain effect on reducing triglyceride, which, based on speculation, is related to the dosage and compatibility of Coptidis Rhizoma; each prescription group has an effect on increasing high-density lipoprotein to a certain degree; and each prescription group has an effect on reducing low-density lipoprotein to a certain degree, wherein the prescription groups 3 and 6 can significantly reduce low density lipoprotein.

The results of comprehensive analysis of the 5 indicators of blood lipids indicate that the effect of regulating blood lipids in Prescription group 6 was the best.

4 Pharmacodynamic Test Results of Comparative Examples
4.1 Measurement Method of Comparative Examples Blood lipid measurement and euglycemic clamp test after 4 weeks of high-fat feeding, and analysis of grouping results and general situation of each group were carried out in accordance with the methods in sections 2.5, 2.6, and 3.1-3.4.

4.2 Blood Glucose Change Situation of Each Comparative Example Group after Treatment After 4 weeks of continuous administration in the same way as that in section 3.5, the test rats fasted overnight for 12 hours, and fasting blood glucose was measured (measured by using glucose meter+blood glucose test strip). The results are shown in Table 8:

TABLE 8

Fasting blood glucose values of each group

| Group | Number of animals | Blood glucose (mmol/L) |
|---|---|---|
| Control group | 12 | 5.12 ± 0.30*** |
| Example 6 | 13 | 13.51 ± 3.26*** |
| Comparative example 1 | 13 | 19.01 ± 2.95 |
| Comparative example 2 | 12 | 16.02 ± 3.10* |
| Comparative example 3 | 12 | 15.22 ± 2.88** |
| Comparative example 4 | 13 | 17.01 ± 3.86 |
| Comparative example 5 | 13 | 18.25 ± 3.77 |
| Model group | 11 | 19.92 ± 3.32 |

(Compared with model group*$P < 0.001$, $P < 0.01$, *$P < 0.05$)

As shown in Table 8, compared with that of the model group, the fasting blood glucose of Example 6 (prescription group 6), and Comparative examples 2 and 3 reduced significantly, wherein the reduction in Example 6 is most significant ($P<0.001$), and the glucose reduction effect in Comparative example 1 is poorest, which is close to that of the model group.

4.3 Blood Lipid Change Situation in Each Comparative Example Group after Treatment After the blood glucose was measured according to the same method as that in section 3.6, the animals in each group were executed by bleeding from the femoral artery, blood samples were collected, serum was separated out, and 5 indicators of blood lipids were measured according to the above methods. The results are shown in the following table:

TABLE 9

Blood lipid values of each group measure after treatment (μmol/L)

| Group | Triglycerides | Free cholesterol | Total cholesterol | High density lipoprotein | Low density lipoprotein |
|---|---|---|---|---|---|
| Control group | 651.22 ± 158.30*** | 71.53 ± 17.14*** | 131.58 ± 29.15*** | 668.13 ± 146.16* | 838.60 ± 152.32** |
| Example 6 | 779.32 ± 216.21** | 128.87 ± 22.66** | 197.13 ± 55.01** | 655.43 ± 121.11* | 860.63 ± 221.51** |
| Comparative example 1 | 885.33 ± 241.25* | 141.23 ± 25.86* | 283.56 ± 59.88* | 552.28 ± 136.56* | 975.32 ± 312.50* |
| Comparative example 2 | 801.77 ± 225.32* | 138.74 ± 27.21* | 276.23 ± 56.74* | 621.02 ± 169.15* | 920.84 ± 297.27* |
| Comparative example 3 | 818.54 ± 232.65* | 146.32 ± 26.22 | 296.30 ± 55.13 | 541.30 ± 179.21 | 989.13 ± 241.55 |

TABLE 9-continued

Blood lipid values of each group measure after treatment (μmol/L)

| Group | Triglycerides | Free cholesterol | Total cholesterol | High density lipoprotein | Low density lipoprotein |
|---|---|---|---|---|---|
| Comparative example 4 | 926.01 ± 206.43 | 151.77 ± 28.56 | 316.33 ± 57.22 | 536.32 ± 141.32 | 1012.01 ± 286.16 |
| Comparative example 5 | 919.25 ± 235.18 | 153.11 ± 27.38 | 302.50 ± 53.32 | 530.10 ± 151.65 | 996.12 ± 231.23 |
| Model group | 1109.12 ± 223.76 | 168.33 ± 28.07 | 328.33 ± 60.12 | 544.25 ± 136.12 | 1181.17 ± 231.01 |

(Compared with model group*P < 0.001, P < 0.01, *P < 0.05)

As shown in Table 9, compared with those in the model group, triglyceride, free cholesterol, total cholesterol, and low-density lipoprotein in Example 6 were significantly reduced, and high-density lipoprotein was significantly increased, and such the effect was significantly better than that in Comparative examples 1-5. In Comparative example 3, only triglyceride was significantly reduced; and in Comparative examples 4-5, triglyceride, free cholesterol, total cholesterol, and low-density lipoprotein were not significantly reduced and high-density lipoprotein was significantly reduced, having a poorest effect.

Upon comprehensive analysis of Table 8 and Table 9, it is found that the glucose reduction effect of Comparative examples 1 and 4-5 is relatively poor, the lipid-lowering effect of Comparative examples 3-5 is relatively poor, and both the glucose reduction and lipid-lowering effects of Comparative example 2 are poorer than those of Example 6 of the present application. It is proved by Example 6 of the present application that the traditional Chinese medicine extract composition of the present application has excellent effects on both glucose reduction and lipid-lowering.

III. Pharmacodynamic Study of the Traditional Chinese Medicine Extract Composition of the Present Invention Sample source: the traditional Chinese medicine extract composition of the present invention: the extract prepared according to Example 6.

Test animals: KKAy mice from Institute of Medical Experimental Zoology, Chinese Academy of Medical Sciences, C57BL/6J mice from Beijing Huafukang Biotechnology Co., LTD., and SD rats from Beijing Vital River Laboratory Animal Technology Co., Ltd.

(1) Normal C57BL/6J Mice

Female/male normal C57BL/6J mice weighing 18-20 g were respectively used as normal control animals for KKAy mice (female) with spontaneous type 2 diabetes and C57BL/6J mice (male) fed with a high-fat diet.

(2) KKAy Mice with Spontaneous Type 2 Diabetes

The female KKAy mice with spontaneous type 2 diabetes were fed with a diet dedicated for KKAy mice, with 5 mice in each cage. When the mice weighed over 40 g, prediction of a plurality of indexes such as blood glucose, blood lipid, and insulin resistance were performed. Based on fasting blood glucose, blood glucose reduction percentage within 40 min in an insulin tolerance test, blood triglyceride (TG), total cholesterol (TC), and weight, the mice were divided into 5 groups, with 12 mice in each group.

(3) C57BL/6J Mice Fed with a High-Fat Diet

The male C57BL/6J mice were fed with a high-fat and high-nutrient diet, with 5 mice in each cage. When the mice weighed over 45 g, prediction of a plurality of indexes such as blood glucose, blood lipid, and insulin resistance were performed. Based on fasting blood glucose, blood glucose reduction percentage within 40 min in an insulin tolerance test, blood TG, blood TC, and weight, the mice were divided into 5 groups, with 12 mice in each group.

Test 1 Effect of the Traditional Chinese Medicine Extract Composition of the Present Invention on Insulin Tolerance of KKay Mice with Spontaneous Type 2 Diabetes The KKAy mice with spontaneous type 2 diabetes were divided into 5 groups based on the following four indexes: blood glucose reduction percentage within 40 min in an insulin tolerance test, fasting blood glucose, blood TG, and blood TC. The groups were respectively a model control group (Con, underwent gavage with a equal volume of water), a positive control drug group (Met, underwent gavage with 150 mg/kg of metformin), and three dosage groups using the traditional Chinese medicine extract composition of the present invention Animals in the three dosage groups underwent gavage with 500, 1000, and 1500 mg/kg of the traditional Chinese medicine extract composition of the present invention respectively, and the active ingredient contents of each dosage group are shown in Table 10.

TABLE 10

Active ingredient contents in different dosage groups using the traditional Chinese medicine extract composition (g/kg)

| Dosage | Total alkaloids | Berberine | Total flavonoids | Neohesperidin | Lovastatin |
|---|---|---|---|---|---|
| 500 mg/kg | 23.525 | 15.79 | 101.8 | 54.15 | 1.295 |
| 1000 mg/kg | 47.05 | 31.58 | 203.6 | 108.3 | 2.59 |
| 1500 mg/kg | 70.575 | 47.37 | 305.4 | 162.45 | 3.885 |

The female C57BL/6J mice were used as a normal animal control group (Nor, underwent gavage with a equal volume of water, n=10). Gavage was performed once a day for 58 consecutive days, and the KKAy mice underwent an insulin tolerance test on the 14th day of administration. On the test day, the animals fasted for 4 hours (free to drink water), blood was collected from the tail tip (0 min), and then regular insulin (0.4 U/kg) was injected subcutaneously, and blood was collected 40 and 90 min after the injection. The blood glucose level was measured using the glucose oxidase method (the same below), and the area under the blood glucose curve (AUC) was calculated.

The results (in Table 11 and Table 12) indicate that blood glucose of the model control group (Con) almost did not reduce after 40 minutes of subcutaneous injection of insulin (0.4 U/kg), indicating that the KKAy mice with spontaneous type 2 diabetes had obvious insulin resistance. Compared with the Con group, the blood glucose of the mice in the three dosage groups using 500, 1000 and 1500 mg/kg of the traditional Chinese medicine extract composition of the present invention decreased at 0 min and 40 min after insulin injection, and the area under the blood glucose curve decreased by 7.8%, 26.1% and 41.8% respectively, presenting a dosage-effect relationship. It is suggested that the traditional Chinese medicine extract composition of the present invention can improve the insulin resistance state of KKAy mice with spontaneous type 2 diabetes to a certain extent.

TABLE 11

Effect of the traditional Chinese medicine composition of the present invention on insulin tolerance in KKAy mice with spontaneous type 2 diabetes

| Group | Dosage (mg/kg) | Blood glucose (mg/dL) | | |
|---|---|---|---|---|
| | | 0 min | 40 min | 90 min |
| Nor | — | 91.1 ± 5.7 | 54.4 ± 12.6 | 60.6 ± 11.5 |
| Con | — | 215.4 ± 71.0 | 198.1 ± 50.3 | 210.7 ± 95.9 |
| Met | 150 | 132.6 ± 32.5** | 115.3 ± 24.2*** | 120.1 ± 25.6** |
| Traditional Chinese medicine composition of the present invention | 500 | 193.9 ± 44.6 | 184.9 ± 41.4 | 194.0 ± 70.9 |
| | 1000 | 153.5 ± 61.3* | 151.9 ± 54.0* | 150.2 ± 52.8 |
| | 1500 | 120.8 ± 50.6** | 117.6 ± 50.1*** | 122.1 ± 65.2* |

(Compared with the model group, n = 12, *P < 0.05, P < 0.01, *P < 0.001)

TABLE 12

Effect of the traditional Chinese medicine composition on the area under the glucose-insulin tolerance curve (AUC) of KKAy mice

| Group | Dosage (mg/kg) | AUC (mg/dL · h) | Change in AUC (%) |
|---|---|---|---|
| Nor | — | 96.4 ± 14.7 | — |
| Con | — | 308.2 ± 95.9 | — |
| Met | 150 | 180.7 ± 36.7*** | ↓41.4 |
| Traditional Chinese medicine composition of the present invention | 500 | 284.1 ± 69.8 | ↓7.8 |
| | 1000 | 227.7 ± 80.7* | ↓26.1 |
| | 1500 | 179.3 ± 79.4** | ↓41.8 |

(Compared with the model group, n = 12, *P < 0.05, P < 0.01, *P < 0.001)

Test 2 Effect of the Traditional Chinese Medicine Extract Composition on Oral Glucose Tolerance of KKAy Mice with Spontaneous Type 2 Diabetes.

The KKAy mice with spontaneous type 2 diabetes were divided into 5 groups based on the following five indexes: blood glucose reduction percentage within 40 min in an insulin tolerance test, fasting blood glucose, blood TG, blood TC, and weight. The groups were respectively a model control group (Con, underwent gavage with a equal volume of water), a positive control drug group (Met, underwent gavage with 150 mg/kg of metformin), and three dosage groups using the traditional Chinese medicine extract composition of the present invention. Animals in the three dosage groups underwent gavage with 500, 1000, and 1500 mg/kg of the traditional Chinese medicine extract composition of the present invention respectively. The female C57BL/6J mice were used as a normal animal control group (Nor, underwent gavage with a equal volume of water, n=10). Gavage was performed once a day for 58 consecutive days, and the aminals in each group underwent an oral glucose tolerance test on the 28th day of administration. On the test day, the animals in each group fasted for 4 hours (free to drink water), blood was collected from the tail tip (0 min), then gavage with a glucose solution was performed (2.0 g/kg), and blood was collected 30, 60, and 120 min after glucose loading. The blood glucose level was measured, and the area under the blood glucose curve (AUC) was calculated.

The results (in Table 13 and Table 14) indicate that, compared with the normal control group (Nor), the blood glucose level of the model control group (Con) significantly increased after the gavage with glucose, indicating an obvious abnormality in the glucose resistance of the KKAy mice with spontaneous type 2 diabetes. Compared with the Con group, the blood glucose of the mice in the three dosage groups using 500, 1000 and 1500 mg/kg of the traditional Chinese medicine extract composition of the present invention decreased to a certain degree after the oral glucose loading, and the area under the blood glucose curve decreased by 12%, 12.5% and 17.2% respectively, wherein the glucose reduction effect in the 1500 mg/kg dosage group has a statistic difference. It is suggested that the traditional Chinese medicine extract composition of the present invention can improve the glucose resistance abnormality of KKAy mice with spontaneous type 2 diabetes to a certain extent.

TABLE 13

Effect of the Chinese medicine composition on oral glucose tolerance of KKAy mice with spontaneous type 2 diabetes

| Group | Dosage (mg/kg) | Blood glucose (mg/dL) | | | |
|---|---|---|---|---|---|
| | | 0 min | 40 min | 90 min | 120 min |
| Nor | — | 98.5 ± 17.3 | 166.4 ± 21.6 | 137.1 ± 17.6 | 114.8 ± 11.6 |
| Con | — | 256.0 ± 49.3 | 434.3 ± 65.3 | 358.8 ± 102 | 306.1 ± 83.4 |
| Met | 150 | 174.7 ± 41.5*** | 292.3 ± 67.3*** | 275.3 ± 70.5* | 271.3 ± 107.1 |
| Traditional Chinese medicine composition of the present invention | 500 | 201.1 ± 73.2* | 407.1 ± 49.7 | 303.5 ± 62.3 | 274.2 ± 91.3 |
| | 1000 | 209.6 ± 59.7* | 388.8 ± 50.3 | 304.7 ± 60.9 | 279.7 ± 57.4 |
| | 1500 | 179.6 ± 54.5** | 376.5 ± 60.5* | 294.0 ± 73.7 | 257.5 ± 51.8 |

(Compared with the model group, n = 10-12, *P < 0.05, P < 0.01, *P < 0.001)

TABLE 14

Effect of the traditional Chinese medicine composition on the
area under the glucose tolerance curve (AUC) of KKAy mice

| Group | Dosage (mg/kg) | AUC (mg/dL · h) | Change in AUC(%) |
|---|---|---|---|
| Nor | — | 268.0 ± 24.8 | — |
| Con | — | 703.2 ± 144.5 | — |
| Met | 150 | 532.0 ± 142.4** | ↓24.4 |

TABLE 14-continued

Effect of the traditional Chinese medicine composition on the
area under the glucose tolerance curve (AUC) of KKAy mice

| Group | Dosage (mg/kg) | AUC (mg/dL · h) | Change in AUC(%) |
|---|---|---|---|
| Traditional Chinese medicine composition of the present invention | 500 | 618.5 ± 122.2 | ↓12.0 |
|  | 1000 | 615.2 ± 91.2 | ↓12.5 |
|  | 1500 | 582.4 ± 113.5* | ↓17.2 |

(Compared with the model group, n = 10-12, *P < 0.05, **P < 0.01)

Test 3 Effect of the Traditional Chinese Medicine Extract Composition of the Present Invention on Fasting Blood Glucose, Blood Insulin Level, and Insulin Sensitivity Index of KKAy Mice with Spontaneous Type 2 Diabetes The KKAy mice with spontaneous type 2 diabetes were divided into 5 groups based on the following five indexes: blood glucose reduction percentage within 40 min in an insulin tolerance test, fasting blood glucose, blood TG, blood TC, and weight. The groups were respectively a model control group (Con, underwent gavage with a equal volume of water), a positive control drug group (Met, underwent gavage with 150 mg/kg of metformin), and three dosage groups using the traditional Chinese medicine extract composition of the present invention. Animals in the three dosage groups underwent gavage with 500, 1000, and 1500 mg/kg of the traditional Chinese medicine extract composition of the present invention respectively. The female C57BL/6J mice were used as a normal animal control group (Nor, underwent gavage with a equal volume of water, n=10). Gavage was performed once a day for 58 consecutive days, and fasting blood glucose and blood insulin level were measured (ELISA method) at the same time when a glucose tolerance test was carried out on the animals in each group on the 28$^{th}$ day of administration, and an insulin sensitivity index (ISI) was calculated, wherein ISI=1/(FBG$_{mg/dl}$× FBI$_{ng/ml}$).

The results (in Table 15) indicate that compared with the Con group, the 500 mg/kg dosage group and the 1500 mg/kg dosage group of the traditional Chinese medicine extract composition of the present invention could significantly reduce the fasting blood glucose and the blood insulin level of the KKAy mice with spontaneous type 2 diabetes, thus significantly increasing the insulin sensitivity index (ISI) thereof.

TABLE 15

Effect of the traditional Chinese medicine composition of the present invention
on fasting blood glucose, insulin, and insulin sensitivity index of KKAy mice

| Group | Dosage (mg/kg) | Blood glucose (mg/dL) | Blood insulin (ng/ml) | ISI (×10$^{-3}$) |
|---|---|---|---|---|
| Nor | — | 98.5 ± 17.3*** | 0.73 ± 0.01*** | 14.2 ± 2.5*** |
| Con | — | 256.0 ± 49.3 | 53.7 ± 33.3 | 0.11 ± 0.09 |
| Met | 150 | 174.7 ± 41.5*** | 36.3 ± 27.6 | 0.26 ± 0.16* |
| Traditional Chinese medicine composition of the present invention | 500 | 201.1 ± 73.2* | 28.5 ± 13.9* | 0.24 ± 0.15* |
|  | 1000 | 209.6 ± 59.7* | 42.9 ± 26.7 | 0.17 ± 0.11 |
|  | 1500 | 179.6 ± 54.5** | 30.7 ± 13.9* | 0.25 ± 0.15* |

(Compared with the model group, n = 10-12, *P < 0.05, P < 0.01, *P < 0.001)

Test 4 Effect of Long-Term Administration of the Traditional Chinese Medicine Extract Composition on Fasting Blood Glucose of KKAy Mice with Spontaneous Type 2 Diabetes at Different Times The KKAy mice with spontaneous type 2 diabetes were divided into 5 groups based on the following five indexes: blood glucose reduction percentage within 40 min in an insulin tolerance test, fasting blood glucose, blood TG, blood TC, and weight. The groups were respectively a model control group (Con, underwent gavage with a equal volume of water), a positive control drug group (Met, underwent gavage with 150 mg/kg of metformin), and three dosage groups using the traditional Chinese medicine extract composition of the present invention. Animals in the three dosage groups underwent gavage with 500, 1000, and 1500 mg/kg of the traditional Chinese medicine extract composition of the present invention respectively. The female C57BL/6J mice were used as a normal animal control group (Nor, underwent gavage with a equal volume of water, n=10). Gavage was performed once a day for 58 consecutive days, the animals in each group fasted for 4 h (free to drink water) on the 14$^{th}$, 21$^{st}$, 28$^{th}$ and 40$^{th}$ day of administration, and blood was collected from the tail tip to measure the fasting blood glucose level.

The results (in table 16) indicate that compared with the Con group, the three dosage groups of 500, 1000, and 1500 mg/kg of the traditional Chinese medicine extract composition of the present invention each can reduce the fasting blood glucose of the KKAy mice with spontaneous type 2 diabetes to different degrees during the administration process, wherein the 1500 mg/kg dosage group reduced the blood glucose of the KKAy mice with spontaneous type 2 diabetes by 43.9%, 23.6%, 29.8% and 22.4% at different times respectively. It is suggested that the continuous administration of the traditional Chinese medicine extract composition of the present invention can obviously control the blood glucose level of the KKAy mice with spontaneous type 2 diabetes.

TABLE 16

Effect of long-term administration of the traditional Chinese medicine composition on the fasting blood glucose level of KKAy mice with spontaneous type 2 diabetes

| Group | Dosage (mg/kg) | Blood glucose (mg/dL) | | | |
|---|---|---|---|---|---|
| | | 14th day after administration | 21st day after administration | 28th day after administration | 40th day after administration |
| Nor | — | — | 125.3 ± 21.5*** | 98.5 ± 17.3*** | 91.0 ± 9.6*** |
| Con | — | 215.4 ± 71.0 | 280.6 ± 62.7 | 256.0 ± 49.3 | 276.8 ± 66.8 |
| Met | 150 | 132.6 ± 32.5** | 176.7 ± 46.2*** | 174.7 ± 41.5*** | 178.5 ± 49.0** |
| Traditional Chinese medicine composition of the present invention | 500 | 193.9 ± 44.6 | 207.4 ± 76.2* | 201.1 ± 73.2* | 221.7 ± 63.6 |
| | 1000 | 153.5 ± 61.3* | 261.4 ± 82.3 | 209.6 ± 59.7* | 232.8 ± 56.8 |
| | 1500 | 120.8 ± 50.1** | 214.1 ± 45.9** | 179.6 ± 59.7** | 214.8 ± 30.5** |

(Compared with the model group, n = 10-12, *P < 0.05, P < 0.01, *P < 0.001)

Test 5 Effect of the Traditional Chinese Medicine Extract Composition of the Present Invention on the Glycosylated Hemoglobin (HbA1c) Level in KKAy Mice with Spontaneous Type 2 Diabetes The KKAy mice with spontaneous type 2 diabetes were divided into 5 groups based on the following five indexes: blood glucose reduction percentage within 40 min in an insulin tolerance test, fasting blood glucose, blood TG, blood TC, and weight. The groups were respectively a model control group (Con, underwent gavage with a equal volume of water), a positive control drug group (Met, underwent gavage with 150 mg/kg of metformin), and three dosage groups using the traditional Chinese medicine extract composition of the present invention. Animals in the three dosage groups underwent gavage with 500, 1000, and 1500 mg/kg of the traditional Chinese medicine extract composition of the present invention respectively. The female C57BL/6J mice were used as a normal animal control group (Nor, underwent gavage with a equal volume of water, n=10). Gavage was performed once a day for 58 consecutive days, and blood was collected from the tail tip on the 48th day to measure the glycosylated hemoglobin level.

The results (in table 17) indicate that, compared with the normal animal control group, the HbA1c level of the KKAy mice with spontaneous type 2 diabetes in the model control group significantly increased. Continuous administration of the traditional Chinese medicine extract composition (500, 1000 and 1500 mg/kg) of the present invention could reduce the HbA1c level in KKAy mice with spontaneous type 2 diabetes by 0.77, 0.87 and 1.03, respectively, wherein there were significant differences between medium and high dosage groups. It is suggested that long-term administration of the traditional Chinese medicine extract composition can significantly control the blood glucose fluctuation of KKAy mice with spontaneous type 2 diabetes.

TABLE 17

Effect of the traditional Chinese medicine composition of the present invention on the glycosylated hemoglobin level in KKAy mice with spontaneous type 2 diabetes (48th day)

| Group | Dosage (mg/kg) | HbA1c (%) |
|---|---|---|
| Nor | — | 2.95 ± 0.12*** |
| Con | — | 5.19 ± 1.04 |
| Met | 150 | 4.34 ± 0.83* |
| Traditional Chinese medicine composition of the present invention | 500 | 4.42 ± 0.71* |
| | 1000 | 4.32 ± 1.15 |
| | 1500 | 4.16 ± 0.72* |

(Compared with the model group, n = 11-12, *P < 0. 05, ***P < 0. 001)

Test 6 Effect of the Traditional Chinese Medicine Extract Composition on the Blood Triglyceride (TG) and Total Cholesterol (TC) Levels in KKAy Mice The KKAy mice with spontaneous type 2 diabetes were divided into 5 groups based on the following five indexes: blood glucose reduction percentage within 40 min in an insulin tolerance test, fasting blood glucose, blood TG, blood TC, and weight. The groups were respectively a model control group (Con, underwent gavage with a equal volume of water), a positive control drug group (Met, underwent gavage with 150 mg/kg of metformin), and three dosage groups using the traditional Chinese medicine extract composition of the present invention Animals in the three dosage groups underwent gavage with 500, 1000, and 1500 mg/kg of the traditional Chinese medicine extract composition of the present invention respectively. The female C57BL/6J mice were used as a normal animal control group (Nor, underwent gavage with a equal volume of water, n=10). Gavage was performed once a day for 58 consecutive days, and at the same time when the animals in each group underwent an insulin tolerance test on the $14^{th}$ day of administration, blood was collected to measure the serum triglyceride (TG) and total cholesterol (TC) levels.

The results (in table 18) indicate that compared to the model control group (Con), the 1500 mg/kg dosage group of the Chinese medicine extract composition of the present invention can significantly reduce the serum TG level of KKAy mice with spontaneous type 2 diabetes, and has no significant influence on the serum TC level.

TABLE 18

Effect of the traditional Chinese medicine composition of the present invention on serum TG and TC levels of KKAy mice with spontaneous type 2 diabetes

| Group | Dosage (mg/kg) | Serum TG (mg/dL) | Serum TC (mg/dL) |
|---|---|---|---|
| Nor | — | 125.8 ± 17.6 | 81.5 ± 47.2 |
| Con | — | 381.5 ± 126.5 | 218.5 ± 38.6 |
| Met | 150 | 253.2 ± 172.6* | 243.8 ± 44.0 |
| Traditional Chinese medicine composition of the present invention | 500 | 392.8 ± 120.2 | 219.4 ± 44.4 |
| | 1000 | 289.4 ± 140.9 | 204.0 ± 53.7 |
| | 1500 | 196.8 ± 76.5*** | 182.4 ± 51.3 |

(Compared with the model group, n = 10-12, *P < 0.05, ***P < 0.001)

Test 7 Effect of Long-Term Administration of the Chinese Medicine Extract Composition of the Present Invention on KKAy Mice with Spontaneous Type 2 Diabetes (Hyperinsulinemic-Euglycemic Clamp Technique)

The KKAy mice with spontaneous type 2 diabetes were divided into 5 groups based on the following five indexes: blood glucose reduction percentage within 40 min in an insulin tolerance test, fasting blood glucose, blood TG, blood TC, and weight. The groups were respectively a model control group (Con, underwent gavage with a equal volume of water), a positive control drug group (Met, underwent gavage with 150 mg/kg of metformin), and three dosage groups using the traditional Chinese medicine extract composition of the present invention. Animals in the three dosage groups underwent gavage with 500, 1000, and 1500 mg/kg of the traditional Chinese medicine extract composition of the present invention respectively. The female C57BL/6J mice were used as a normal animal control group (Nor, underwent gavage with a equal volume of water, n=10). Gavage was performed once a day for 58 consecutive days, and After the $54^{th}$ day of administration to the animals in each group, 5-6 mice were randomly selected from different groups to carry out a hyperinsulinemic-euglycemic clamp test each day.

The results (in table 19) indicate that compared with the normal animal control group (Nor), under the condition of high insulin level, when it reached a blood glucose steady state (6.0 mmol/L), the glucose infusion rate (GIR) of KKAy mice with spontaneous type 2 diabetes in the model control group (Con) was significantly reduced, indicating that the KKAy mice with spontaneous type 2 diabetes have obvious insulin resistance. Compared with the model control group (Con), the three dosage groups of 500, 1000 and 1500 mg/kg of the traditional Chinese medicine extract composition of the present invention can increase the GIR value of KKAy mice with spontaneous type 2 diabetes by 12.3%, 54.3% and 70.4% respectively with long-term administration. It is suggested that the long-term administration of the traditional Chinese medicine extract composition of the present invention can improve the insulin sensitivity of KKAy mice with spontaneous type 2 diabetes.

TABLE 19

Effect of long-term administration of the traditional Chinese medicine composition of the present invention on the glucose infusion rate of KKAy mice with spontaneous type 2 diabetes

| Group | Dosage (mg/kg) | SSBG (mmol/L) | IIR (mU/kg/min) | GIR (mg/kg · min) |
|---|---|---|---|---|
| Nor | — | 6.0 ± 0.3 | 20.0 | 27.2 ± 0.8*** |
| Con | — | 6.0 ± 0.3 | 20.0 | 8.1 ± 2.2 |
| Met | 150 | 6.0 ± 0.3 | 20.0 | 14.5 ± 0.6** |
| Traditional Chinese medicine composition of the present invention | 500 | 6.0 ± 0.3 | 20.0 | 9.1 ± 0.5 |
| | 1000 | 6.0 ± 0.3 | 20.0 | 12.5 ± 4.3 |
| | 1500 | 6.0 ± 0.3 | 20.0 | 13.8 ± 4.6* |

(Compared with the model group, n = 3-5, *P < 0.05, P < 0.01, *P < 0.001)

Test 8 Effect of the Traditional Chinese Medicine Extract Composition of the Present Invention on Blood Pressure of KKAy Mice with Spontaneous Type 2 Diabetes The KKAy mice with spontaneous type 2 diabetes were divided into 5 groups based on the following five indexes: blood glucose reduction percentage within 40 min in an insulin tolerance test, fasting blood glucose, blood TG, blood TC, and weight. The groups were respectively a model control group (Con, underwent gavage with a equal volume of water), a positive control drug group (Met, underwent gavage with 150 mg/kg of metformin), and three dosage groups using the traditional Chinese medicine extract composition of the present invention Animals in the three dosage groups underwent gavage with 500, 1000, and 1500 mg/kg of the traditional Chinese medicine extract composition of the present invention respectively. The female C57BL/6J mice were used as a normal animal control group (Nor, underwent gavage with a equal volume of water, n=10). Gavage was performed once a day for 58 consecutive days, and onOn the $53^{rd}$ day of administration to the animals in each group, the blood pressure was measured by using an intelligent non-invasive sphygmomanometer (BP98A, Beijing Ruanlong Biotechnology Co., Ltd.).

The results (in table 20) indicate that 53 days of continuous administration of the Chinese medicine extract composition of the present invention (500, 1000 and 1500 mg/kg) can significantly reduce the blood pressure of KKAy mice with spontaneous type 2 diabetes (Note: Due to the small weight and thin tail, the blood pressure of mice in the normal control group cannot be measured with a non-invasive sphygmomanometer).

TABLE 20

Effect of the traditional Chinese medicine composition of the present invention on blood pressure of KKAy mice with spontaneous type 2 diabetes

| Group | Dosage (mg/kg) | BP (mmHG) |
|---|---|---|
| Nor | — | — |
| Con | — | 129.4 ± 11.9 |
| Met | 150 | 118.7 ± 10.8* |
| Traditional Chinese medicine composition of the present invention | 500 | 119.1 ± 6.5* |
| | 1000 | 120.3 ± 8.1* |
| | 1500 | 117.1 ± 6.3** |

(Compared with the model group, n = 11-12, *P < 0.05, **P < 0.01)

Test 9 Effect of the Traditional Chinese Medicine Extract Composition of the Present Invention on the Insulin Tolerance of C57BL/6J Mice Fed with a High-Fat Diet C57BL/6J mice fed a with high-fat diet and weighing more than 45 g were selected for multi-index prediction tests such as blood glucose, blood lipids, and insulin resistance, and were divided into 5 groups based on the following five indexes: blood glucose reduction percentage within 40 min in an insulin tolerance test, fasting blood glucose, blood TG, blood TC, and weight, with 12 mice in each group. The groups were respectively a model control group (Con), a metformin positive control group (Met, 150 mg/kg), and three dosage groups (500, 1000, and 1500 mg/kg) using the traditional Chinese medicine extract composition of the present invention. Male C57BL/6J mice were used as a normal animal control group. Animals in the positive drug group and each test drug group underwent gavage with a corresponding dosage of the test drug each day. The normal control group and model group underwent gavage with an equal volume of water once a day for 30 days. Animals in each group underwent an insulin tolerance test on the 10$^{th}$ day of the administration. On the test day, the animals fasted for 4 hours (free to drink water), blood was collected from the tail tip (0 min), and then regular insulin (0.4 U/kg) was injected subcutaneously. The blood was collected 40 min and 90 min after the injection to measure the blood glucose level and calculate AUC.

The results (in table 21 and table 22) indicate that, in comparison of the blood glucose measured 40 minutes after the insulin injection with the blood glucose measured 0 minute after the insulin injection, the blood glucose of C57BL/6J mice in the normal animal control group decreased by 40.3% at 40 min after the insulin injection, and the blood glucose of C57BL/6J mice fed with a high-fat diet in the model control group decreased by 26.7% at 40 min after the insulin injection, indicating that obese C57BL/6J mice had insulin resistance.

Compared with the model control group (Con), in the 500 mg/kg dosage group and the 1500 mg/kg dosage group of the traditional Chinese medicine extract composition of the present invention, the blood glucose and AUC of C57BL/6J mice fed with a high-fat diet measured 40 min and 90 min after the insulin injection significantly decreased, and in the 1000 mg/kg group, the blood glucose and AUC of C57BL/6J mice fed with a high-fat diet measured 90 min after the insulin injection significantly decreased. It is suggested that the traditional Chinese medicine extract composition of the present invention can significantly improve the insulin resistance of C57BL/6J mice fed with a high-fat diet.

Test 10 Effect of Traditional Chinese Medicine Extract Composition of the Present Invention on Oral Glucose Tolerance of C57BL/6J Mice Fed with a High-Fat Diet C57BL/6J mice fed a with high-fat diet and weighing more than 45 g were selected for multi-index prediction tests such as blood glucose, blood lipids, and insulin resistance, and were divided into 5 groups based on the following five indexes: blood glucose reduction percentage within 40 min in an insulin tolerance test, fasting blood glucose, blood TG, blood TC, and weight, with 12 mice in each group. The groups were respectively a model control group (Con), a metformin positive control group (Met, 150 mg/kg), and three dosage groups (500, 1000, and 1500 mg/kg) using the traditional Chinese medicine extract composition of the present invention. Male C57BL/6J mice were used as a normal animal control group Animals in the positive drug group and each test drug group underwent gavage with a corresponding dosage of the test drug each day. The normal control group and model group underwent gavage with an equal volume of water once a day for 30 days Animals in each group underwent a glucose tolerance test on the 29th day of the administration. On the test day, the animals fasted for 4 hours (free to drink water), blood was collected from the tail tip (0 min), and then a glucose solution (2.0 g/kg) was administered by gavage. The blood was collected 30 min, 60 min, and 120 min after the glucose loading to measure the blood glucose level and calculate AUC.

TABLE 21

Effect of the Chinese medicine composition of the present invention on the insulin tolerance of C57BL/6J mice fed with a high-fat diet

| Group | Dosage (mg/kg) | Glu (mg/dL) | | |
|---|---|---|---|---|
| | | 0 min | 40 min | 90 min |
| Nor | — | 91.1 ± 5.7*** | 54.4 ± 12.6*** | 60.6 ± 11.5*** |
| Con | — | 123.0 ± 11.6 | 90.2 ± 12.6 | 91.1 ± 13.9 |
| Met | 150 | 104.5 ± 7.6*** | 78.3 ± 10.3* | 87.5 ± 24.6 |
| Traditional Chinese medicine composition of the present invention | 500 | 113.9 ± 13.0 | 75.1 ± 8.7*** | 76.3 ± 7.6** |
| | 1000 | 112.9 ± 15.8 | 77.9 ± 17.1 | 75.4 ± 20.4* |
| | 1500 | 113.3 ± 13.9 | 79.1 ± 11.0* | 74.4 ± 8.1** |

(Compared with the model group, n = 10-12, *P < 0.05, P < 0.01, *P < 0.001)

TABLE 22

Effect of the Chinese medicine composition of the present invention on insulin tolerance AUC of C57BL/6J mice fed with a high-fat diet

| Group | Dosage (mg/kg) | AUC (mg/dL · h) | Change in AUC (%) |
|---|---|---|---|
| Nor | — | 96.4 ± 14.7 | — |
| Con | — | 146.6 ± 15.6 | — |
| Met | 150 | 130.0 ± 13.3* | ↓11.4 |
| Traditional Chinese medicine composition of the present invention | 500 | 126.0 ± 12.9** | ↓14.0 |
| | 1000 | 127.5 ± 24.8* | ↓13.0 |
| | 1500 | 128.1 ± 13.4** | ↓12.7 |

(Compared with the model group, n = 10-12, *P < 0.05, **P < 0.01)

The results (in table 23 and table 24) indicate that, in the 500 mg/kg dosage group and the 1000 mg/kg dosage group of the traditional Chinese medicine extract composition of the present invention, the blood glucose of C57BL/6J mice fed with a high-fat diet measured 30, 60, and 120 minutes after the oral glucose loading significantly decreased; in the 1500 mg/kg dosage group, the blood glucose measured 30 minutes after the glucose loading significantly decreased; and in the three dosage groups, AUC respectively decreased by 10.5%, 14.8% and 1.7%. It is suggested that the traditional Chinese medicine extract composition of the present invention could improve the abnormal state of oral glucose tolerance of C57BL/6J mice fed with a high-fat diet.

TABLE 23

Effect of the traditional Chinese medicine composition of the present invention
on oral glucose tolerance of C57BL/6J mice fed with a high-fat diet

| Group | Dosage (mg/kg) | Glu (mg/dL) | | | |
|---|---|---|---|---|---|
| | | 0 min | 30 min | 60 min | 120 min |
| Nor | — | 88.0 ± 7.1 | 151.0 ± 23.5 | 107.9 ± 17.9 | 90.4 ± 10.7 |
| Con | — | 120.3 ± 13.9 | 189.2 ± 24.6 | 148.8 ± 8.2 | 117.2 ± 18.2 |
| Met | 150 | 107.1 ± 13.9* | 162.8 ± 17.3** | 140.0 ± 19.5 | 108.8 ± 16.7 |
| Traditional Chinese medicine composition of the present invention | 500 | 120.4 ± 17.3 | 159.4 ± 19.4** | 138.7 ± 14.0* | 100.5 ± 15.3* |
| | 1000 | 114.8 ± 21.1 | 142.3 ± 22.0*** | 136.3 ± 19.1* | 98.5 ± 22.2* |
| | 1500 | 119.0 ± 17.1 | 164.2 ± 18.4* | 161.2 ± 19.7 | 114.4 ± 22.1 |

(Compared with the model group, n = 10-12, *P < 0.05, P < 0.01, *P < 0.001)

TABLE 24

Effect of the Chinese medicine composition of
the present invention on oral glucose tolerance
AUC of C57BL/6J mice fed with a high-fat diet

| Group | Dosage (mg/kg) | AUC (mg/dL · h) | Change in AUC (%) |
|---|---|---|---|
| Nor | — | 223.6 ± 22.1 | — |
| Con | — | 294.9 ± 18.3 | — |
| Met | 150 | 267.6 ± 21.5** | ↓9.3 |
| Traditional Chinese medicine composition of the present invention | 500 | 264.0 ± 23.1** | ↓10.5 |
| | 1000 | 251.3 ± 30.7*** | ↓14.8 |
| | 1500 | 290.0 ± 27.9 | ↓1.7 |

(Compared with the model group, n = 10-12, P < 0.01, *P < 0.001)

In the pharmacodynamic tests, obese KKAy mice with spontaneous type 2 diabetes and having insulin resistance and C57BL/6J mice fed with a high-fat diet were used as experimental animal models, to investigate the effects of the Chinese medicine extract composition of the present invention on metabolic syndrome-related indicators such as insulin resistance, glucose and lipid metabolism, blood pressure, and body weight.

The results of the pharmacodynamic tests indicate that the traditional Chinese medicine extract composition of the present invention has the following effects: (1) reducing blood glucose; (2) reducing the blood insulin level; (3) improving the impaired oral glucose tolerance; (4) reducing glycosylated hemoglobin (HbA1c); (5) increasing the insulin sensitivity index and improving the body insulin resistance; (6) reducing the blood triglyceride level, and having a tendency to reduce the total cholesterol; and (7) lowering the blood pressure.

IV. The Safety of the Traditional Chinese Medicine Extract Composition of the Present Invention Test animals: C57BL/6J mice from Beijing Huafukang Biotechnology Co., LTD., and Beagle dogs from Beijing Maas Biotechnology Co., LTD.

In the oral administration-based acute toxicity test on mice of the traditional Chinese medicine extract composition of the present invention, it is measured that $LD_{50}$ is greater than 20000 mg/kg.

In the oral administration-based acute toxicity test on Beagle dogs of the traditional Chinese medicine extract composition of the present invention, it is measured that a lethal dosage is greater than 7500 mg/kg, and a main toxic reaction is vomiting after administration. The dosage of 20000 mg/kg is 200 times of the clinically planned dosage, and the dosage of 7500 mg/kg is 75 times of the clinically planned dosage.

In the oral administration-based long-term toxicity test on rats of the traditional Chinese medicine extract composition of the present invention, the results indicate that: the traditional Chinese medicine extract composition of the present invention may cause restorable gastric injuries such as forestomach hyperkeratosis and parakeratosis, and mucosal destruction in rats; and liver damages such as reversible hepatocellular hypertrophy and refractory bile duct hyperplasia. The dosages in the long-term toxicity test are 8, 28, 98 times of the clinically planned dosage, and the toxic effect is closely related to the long-term use of the test product in large dosages and the solvent used to prepare the test product. Therefore, the clinically planned dosage of the traditional Chinese medicine extract composition of the present invention is safe.

The above descriptions are only specific embodiments of the present invention, but the protection scope of the present invention is not limited thereto, any changes or substitutions that can be easily conceived by those skilled in the art within the technical scope disclosed by the present invention should be covered by the protection scope of the present invention. Therefore, the protection scope of the present invention should be subjected to the protection scope of the claims.

Practicality

The traditional Chinese medicine composition and the traditional Chinese medicine extract composition provided according to the embodiments of the present invention are applicable to the technical field of medicines, and are particularly applicable to the treatment of metabolic syndrome.

What is claimed is:

1. A traditional Chinese medicine extract composition, prepared by mixing extracts of Coptidis Rhizoma, Aurantii Fructus Immaturus, red yeast rice, and one or more selections from the group consisting of Pinelliae Rhizoma, Trichosanthis Fructus, and Cinnamomi Cortex as active ingredients,
   wherein the composition is a tablet, capsule, granule, or liquid comprising 1-15 g of the active ingredients,
   wherein the traditional Chinese medicine extract composition contains the following active ingredients (mg/g): 6-122 mg/g of total alkaloids, 30-315 mg/g of total flavonoids, and 0.5-9 mg/g of lovastatin,
   wherein the total alkaloids comprise four alkaloids: berberine hydrochloride, jatrorrhizine hydrochloride, coptisine hydrochloride, and Barmartine hydrochloride, and
   the total flavonoids comprise three flavonoid glycosides: neohesperidin, hesperidin, and naringin.

2. The traditional Chinese medicine extract composition according to claim 1, wherein the Coptidis Rhizoma extract accounts for 2-30%, and the extracts of the remaining active ingredients account for 70-98% of the active ingredients.

3. A method for preparing the traditional Chinese medicine extract composition according to claim 1, wherein:
- (a-1) Coptidis Rhizoma is extracted by using acid water, and filtration, concentration, alkali precipitation, salting-out, filtration, drying, pulverization are performed to prepare a total alkaloids extract of Coptidis Rhizoma;
- (a-2) four medicinal materials consisting of: 10-100% of a prescribed dosage of red yeast rice, Aurantii Fructus Immaturus, Pinelliae Rhizoma, and Cinnamomi Cortex, are extracted by using 50-90% ethanol, and filtration is performed;
- (a-3) Trichosanthis Fructus is extracted by using 75-95% ethanol, a Trichosanthis Fructus extraction solution is merged with an extraction solution of the four traditional Chinese medicinal materials, decompression is performed to recover ethanol, concentration, drying, and pulverization are performed to prepare a mixed extract of five traditional Chinese medicinal materials consisting of: Aurantii Fructus Immaturus, Pinelliae Rhizoma, red yeast rice, Cinnamomi Cortex, and Trichosanthis Fructus; and
- (a-4) the total alkaloids extract of Coptidis Rhizoma, the mixed extract of the five traditional Chinese medicinal materials, and 0-90% of the prescribed dosage of red yeast rice fine powder are well mixed to prepare the traditional Chinese medicine extract composition.

4. A pharmaceutical preparation comprising the traditional Chinese medicine extract composition according to claim 1 in a form of injections, tablets, capsules, granules, and oral liquids.

5. A method of treating a patient comprising administering to the patient a therapeutically effective dosage of the traditional Chinese medicine extract composition according to claim 1, wherein the method is a method of:
- a. treating one or a plurality of the following: metabolic syndrome, obesity, hyperglycemia, hyperlipidemia, and hypertension;
- b. treating one or a plurality of the following: disorder of blood glucose and lipid metabolism, obesity, hyperglycemia, hyperlipidemia, and hypertension, in the early stage of metabolic syndrome;
- c. achieving one or a plurality of the following: reducing blood glucose, reducing the hypoglycemic insulin level, improving oral glucose tolerance abnormality, reducing the glycated hemoglobin (HbA1c) level, increasing the insulin sensitivity index, improving insulin resistance, reducing the blood triglyceride level, reducing total cholesterol, and reducing the blood pressure; or
- d. achieving major functions: clearing heat, eliminating phlegm, and promoting qi circulation to relieve distension; and treating symptoms caused by the stagnation of phlegm-heat, such as obesity, enlarged abdomen, chest distress, excessive phlegm, inappetence and feeling of fullness in stomach and abdomen, dry mouth, thirst, polydipsia, and easy hunger, irritability, flushing and oily face, snoring at night, loose or dry stool, yellow urine, red tongue with yellow coating and slippery pulse.

6. The traditional Chinese medicine composition according to claim 1, wherein the Aurantii Fructus Immaturus is Aurantii Fructus Immaturus parched with bran, the Pinelliae Rhizoma is Pinelliae Rhizoma Praeparatumcum Zingibere Et Alumine, and the Trichosanthis Fructus is whole Trichosanthis Fructus.

7. The traditional Chinese medicine composition according to claim 1, wherein the composition comprises 14-38 g of the active ingredients.

8. The traditional Chinese medicine composition according to claim 1, wherein the composition comprises 5-80 wt % of Coptidis Rhizoma, 5-70 wt % of Aurantii Fructus Immaturus, 10-60 wt % of Pinelliae Rhizoma, 5-40 wt % of Trichosanthis Fructus, 2-12 wt % of Cinnamomi Cortex, and 10-60 wt % of red yeast rice.

9. The traditional Chinese medicine composition according to claim 8, wherein the composition comprises 10-30 wt % of Coptidis Rhizoma, 10-30 wt % of Aurantii Fructus Immaturus, 10-30 wt % of Pinelliae Rhizoma, 5-30 wt % of Trichosanthis Fructus, 2-10 wt % of Cinnamomi Cortex, and 12-36 wt % of red yeast rice.

10. The traditional Chinese medicine composition according to claim 9, wherein the composition comprises 19.6 wt % of Coptidis Rhizoma, 19.6 wt % of Aurantii Fructus Immaturus, 19.6 wt % of Pinelliae Rhizoma, 26.1 wt % of Trichosanthis Fructus, 2.1 wt % of Cinnamomi Cortex, and 13.0 wt % of red yeast rice.

11. The traditional Chinese medicine extract composition according to claim 1, wherein the daily administration dosage of the traditional Chinese medicine extract composition is 2-10 g.

12. The traditional Chinese medicine extract composition according to claim 2, wherein the Coptidis Rhizoma extract accounts for 3-25%, and the extracts of the remaining traditional Chinese medicinal materials account for 75-97%.

13. The traditional Chinese medicine extract composition according to claim 12, wherein the Coptidis Rhizoma extract accounts for 5-15%, and the extracts of the remaining traditional Chinese medicinal materials account for 85-95%.

14. The traditional Chinese medicine extract composition according to claim 1, wherein the traditional Chinese medicine extract composition contains as active ingredients (mg/g): 6-122 mg/g of total alkaloids, which comprise 4-89 mg/g of berberine; 30-315 mg/g of total flavonoids, which comprise 20-186 mg/g of neohesperidin; and 0.5-9 mg/g of lovastatin.

* * * * *